United States Patent
Aftab et al.

(10) Patent No.: US 10,166,225 B2
(45) Date of Patent: Jan. 1, 2019

(54) METHOD FOR TREATING OSTEOPOROSIS

(71) Applicant: Exelixis, Inc., South San Francisco, CA (US)

(72) Inventors: Dana T. Aftab, San Rafael, CA (US); Douglas Clary, San Francisco, CA (US)

(73) Assignee: Exelixis, Inc., Alameda, CA (US)

( * ) Notice: Subject to any disclaimer, the term of this patent is extended or adjusted under 35 U.S.C. 154(b) by 510 days.

(21) Appl. No.: 14/346,570

(22) PCT Filed: Sep. 20, 2012

(86) PCT No.: PCT/US2012/056281
§ 371 (c)(1),
(2) Date: Mar. 21, 2014

(87) PCT Pub. No.: WO2013/043840
PCT Pub. Date: Mar. 28, 2013

(65) Prior Publication Data
US 2014/0228401 A1   Aug. 14, 2014

Related U.S. Application Data

(60) Provisional application No. 61/538,039, filed on Sep. 22, 2011.

(51) Int. Cl.
*A61K 31/47* (2006.01)
*G01N 33/68* (2006.01)
*A61K 9/20* (2006.01)

(52) U.S. Cl.
CPC ............ *A61K 31/47* (2013.01); *A61K 9/2018* (2013.01); *A61K 9/2054* (2013.01); *G01N 33/6887* (2013.01); *G01N 2333/78* (2013.01); *G01N 2333/916* (2013.01); *G01N 2800/108* (2013.01); *G01N 2800/52* (2013.01)

(58) Field of Classification Search
CPC ........................................................ A61K 31/47
USPC ........................................................ 514/312
See application file for complete search history.

(56) References Cited

U.S. PATENT DOCUMENTS

| | | |
|---|---|---|
| 7,579,473 B2 | 8/2009 | Bannen et al. |
| 7,977,345 B2 | 7/2011 | Bannen et al. |
| 7,999,006 B2 | 8/2011 | Lamb |
| 8,067,436 B2 | 11/2011 | Bannen et al. |
| 8,178,532 B2 | 5/2012 | Bannen et al. |
| 8,476,298 B2 | 7/2013 | Bannen et al. |
| 8,497,284 B2 | 7/2013 | Bannen et al. |

(Continued)

FOREIGN PATENT DOCUMENTS

| | | |
|---|---|---|
| WO | 2006014325 | 2/2006 |
| WO | 2006108059 | 12/2006 |

(Continued)

OTHER PUBLICATIONS

Susa, et al, TiPS—Dec. 2000 (vol. 21) 489.*

(Continued)

*Primary Examiner* — Shengjun Wang
(74) *Attorney, Agent, or Firm* — Honigman Miller Schwartz and Cohn LLP; Heidi M. Berven; Jonathan P. O'Brien

(57) ABSTRACT

This invention is directed to the treatment of osteoporosis using N-(4-{[6,7-bis(methyloxy)quinolin-4-yl]oxy}phenyl)-N'-(4-fluorophenyl)cyclopropane-1,1-dicarboxamide.

9 Claims, 6 Drawing Sheets

(56) References Cited

U.S. PATENT DOCUMENTS

| | | |
|---|---|---|
| 8,673,912 B2 | 3/2014 | Cannon et al. |
| 8,877,776 B2 | 11/2014 | Brown et al. |
| 9,174,947 B2 | 11/2015 | Bannen et al. |
| 9,365,516 B2 | 6/2016 | Wilson et al. |
| 9,717,720 B2 | 8/2017 | Wilson et al. |
| 9,724,342 B2 | 8/2017 | Wilson et al. |
| 2008/0161305 A1 | 7/2008 | Forsyth et al. |
| 2009/0274693 A1 | 11/2009 | Gilmer et al. |
| 2011/0077233 A1 | 3/2011 | Bannen et al. |
| 2012/0070368 A1 | 3/2012 | Bannen et al. |
| 2012/0184523 A1 | 7/2012 | Bannen et al. |
| 2012/0252840 A1 | 10/2012 | Aftab et al. |
| 2012/0282179 A1 | 11/2012 | Aftab et al. |
| 2013/0030172 A1 | 1/2013 | Wilson et al. |
| 2013/0142790 A1 | 6/2013 | Gilmer et al. |
| 2013/0143881 A1 | 6/2013 | Cannon et al. |
| 2013/0150363 A1 | 6/2013 | Gilmer et al. |
| 2013/0197230 A1 | 8/2013 | Wilson et al. |
| 2013/0252940 A1 | 9/2013 | Bannen et al. |
| 2013/0252956 A1 | 9/2013 | Kallender et al. |
| 2013/0330377 A1 | 12/2013 | Wilson |
| 2014/0057908 A1 | 2/2014 | Smith et al. |
| 2014/0057943 A1 | 2/2014 | Smith et al. |
| 2014/0066444 A1 | 3/2014 | Smith et al. |
| 2014/0121239 A1 | 5/2014 | Aftab |
| 2014/0155396 A1 | 6/2014 | Bannen et al. |
| 2014/0179736 A1 | 6/2014 | Schwab et al. |
| 2014/0228401 A1 | 8/2014 | Aftab et al. |
| 2014/0256938 A1 | 9/2014 | Wilson et al. |
| 2014/0302012 A1 | 10/2014 | Aftab et al. |
| 2014/0323522 A1 | 10/2014 | Aftab et al. |
| 2015/0057310 A1 | 2/2015 | Brown et al. |
| 2015/0133494 A1 | 5/2015 | Aftab et al. |
| 2015/0196545 A1 | 7/2015 | Aftab et al. |
| 2015/0202196 A1 | 7/2015 | Bannen et al. |
| 2015/0238477 A1 | 8/2015 | Aftab |
| 2015/0376133 A1 | 12/2015 | Bannen et al. |
| 2016/0000772 A1 | 1/2016 | Aftab et al. |
| 2016/0051532 A1 | 2/2016 | Aftab et al. |
| 2016/0185725 A1 | 6/2016 | Bannen et al. |
| 2016/0220554 A1 | 8/2016 | Smith et al. |
| 2016/0229805 A1 | 8/2016 | Wilson et al. |
| 2017/0057921 A1 | 3/2017 | Wilson et al. |
| 2017/0143689 A1 | 5/2017 | Wilson et al. |
| 2017/0266178 A1 | 9/2017 | Wilson et al. |
| 2017/0275251 A1 | 9/2017 | Brown et al. |
| 2018/0002289 A1 | 1/2018 | Brown et al. |
| 2018/0037552 A1 | 2/2018 | Brown et al. |

FOREIGN PATENT DOCUMENTS

| | | | | |
|---|---|---|---|---|
| WO | 2008021389 | | 3/2008 | |
| WO | 2009137429 | | 11/2009 | |
| WO | 2010036831 | | 4/2010 | |
| WO | 2010039248 | A1 | 4/2010 | |
| WO | 2010056960 | | 5/2010 | |
| WO | 2010083414 | | 7/2010 | |
| WO | 2011009095 | | 1/2011 | |
| WO | 2011112896 | | 9/2011 | |
| WO | 2012009722 | | 1/2012 | |
| WO | 2012009723 | | 1/2012 | |
| WO | WO 2012/031027 | A1 * | 3/2012 | ............ A61K 39/00 |
| WO | 2012044572 | A1 | 4/2012 | |
| WO | 2012044574 | | 4/2012 | |
| WO | 2012044577 | | 4/2012 | |
| WO | 2012071321 | | 5/2012 | |
| WO | 2012109510 | | 6/2012 | |
| WO | 2012151326 | A1 | 11/2012 | |
| WO | 2013059788 | | 4/2013 | |
| WO | 2013070890 | | 5/2013 | |
| WO | 2013070903 | | 5/2013 | |
| WO | 2013166296 | | 11/2013 | |
| WO | 2014039971 | | 3/2014 | |

OTHER PUBLICATIONS

Nenonen, A. et al, Journal of Bone and Mineral Research, vol. 20, No. 8, 2005, p. 1804-1812.*

Lazner, et al., Human Molecular Genetics, 1999, vol. 8. No. 10, Review 1839-1846.*

Torres et al. Clin Cancer Res. Jun. 15, 2011; 17(12): 3943-3955.* http://www.selleckchem.com/products/cabozantinib-malate.html.*

Exelixis, clinical trial No. NCT01553656, Mar. 14, 2012.*

Fuller, et al., "The effect of hepatocyte growth factor on the behavior of osteoclasts", Biochemical and Biophysical Research Communications, 212(2):334-340, 1995.

Hussain, et al., "Cabozantinib (XL184) in metastatic castration-resistant prostate cancer (mCRPC): Results from a phase II randomized discontinuation trial", ASCO Meeting Abstracts, Jun. 9, 2011, retrieved from internet: URL:http://meetinglibrary.asco.org/print/572494 [retrieved on Dec. 3, 2012].

Kuznar, "Cabozantinib shows dramatic effects on bone metastases in advance prostate cancer", American Health and Drug Benefits, 2011, Engage Healthcare Communications, Inc., USA, 4(4): 1942-2962, 2011; and Database Accession No. EMB-2011515121 abstract.

Saylor, et al., "Emerging therapies to prevent skeletal morbidity in men with prostate cancer", Journal of Clinical Oncology, 29(27):3705-3714, 2011.

Smith, et al., "406 Phase 2 study of XL184 in cohort of patients (pts) with castration resistant prostate cancer (CRPC) and measurable soft tissue disease", European Journal of Cancer, Supplement, 8(7):129, 2010.

Yang, et al., "VEGF enhancement of osteoclast survival and bone resorption involves VEGF receptor-2 signaling and beta3-integrin", Matrix Biology, 27(7): 589-599, 2008.

International Search Report for PCT/US2012/056281 dated Dec. 19, 2012.

Schimmoller, F., et al: "Cabozantinib (XL184), a dual MET-VEGFR2 inhibitor, blocks osteoblastic and osteolytic progression of human prostate cancer xenografts in mouse bone" [abstract], Proceedings of the 23rd AACR-NCI-EORTC International Conference: Molecular Targets and Cancer Therapeutics, San Francisco, CA, USA, vol. 10, No. 11, Suppl. 1, Abs. No. A233, Nov. 12-16, 2011.

Anonymous, "Another update on cabozantinib (XL184)", The "New" Prostate Cancer Infolink, Sep. 7, 2011, retrieved from the internet at http://prostatecancerinfolink.net/2011/09/07/another-update-on-cabozantinib-xl184/ on Dec. 21, 2015.

Börset, M., et al., "Hepatocyte Growth Factor and Its Receptor c-Met in Multiple Myeloma", Blood, vol. 88, No. 10, pp. 3998-4004, Sep. 15, 1996.

Elisei, R., et al., "Cabozantinib in Progressive Medullary Thyroid Cancer", Journal of Clinical Oncology, col. 30, No. 29, pp. 3639-3646, Sep. 3, 2013.

FDA Label for Cometriq, Nov. 2012.

FDA Label for Cabometyx, Apr. 2016.

Marino et al., "Osteonecrosis of the jaw in a patient receiving cabozantinib", Australian Dental Journal, vol. 60, No. 4, Nov. 27, 2015.

Osterweil, Neil, "Cabozantinib versus everolimus in advanced RCC with bone mets", Oncology Practice, Feb. 10, 2017, retrieved from www.mdedge.com/oncologypracticel/artide/131183/renal-cell-carcinoma/cabozantinib-versus-everolimus-advanced-rcc on Jun. 30, 2017.

Smith, M., et al., "Abstract: Phase III Study of Cabozantinib in Previously Treated Metastatic Castration-Resistant Prostate Cancer. COMET-1", Journal of Clinical Oncology, Sep. 2016, retrieved from http://ascopubs.org/doi/full/10.1200/JCO.2015.65.5597 on Jun. 30, 2017.

Standal, T., et al., "HGF inhibits BMP-induced osteoblastogenesis: possible implications for the bone disease of multiple myeloma", Blood, vol. 109, No. 7, Apr. 1, 2007.

Zhang, Y., et al., "XL-184, a MET, VEGFR-2 and RET kinase inhibitor for the treatment of thyroid cancer, clioblastoma multiforme and NSCLC", Idrugs, vol. 13, No. 2, pp. 112-121, Feb. 2010.

* cited by examiner

FIG. 6

| Study day | Animals (n = 40) |
|---|---|
| Day -7 | Body weight and blood collection |
| | Randomization to study groups by stratification according to body weight and serum PINP levels |

| Study day during the in-life phase | SHAM (n = 8) | OVX (n = 32, 8 per study group) | | | |
|---|---|---|---|---|---|
| | Vehicle | Vehicle | E2 (4 µg/kg/d s.c.) | cabozantinib (mg/kg/d p.o.) | |
| | | | | 1 | 3 |
| Day 0 | Body weight and surgical SHAM and OVX operations | | | | |
| Daily throughout the in-life phase (up to day 13) | Treatment with cabozantinib, 17β-estradiol and vehicle | | | | |
| Day 7 | Body weight and adjustment of treatment doses according to the body weight | | | | |
| Day 14 | Body weight, blood collection, and relative uterine weight | | | | |

| Experimental analyses | Study day | | | |
|---|---|---|---|---|
| | Day -7 | Day 0 | Day 7 | Day 14 |
| Body weight | x | x | x | x |
| Relative uterine weight | | | | x |
| Bone metabolism biomarkers, including PINP, OC, CTX and TRACP 5b | x | | | x |

METHOD FOR TREATING OSTEOPOROSIS

CROSS-REFERENCE TO RELATED APPLICATIONS

This application is a United States National Phase filing of PCT/US2012/056281, filed Sep. 20, 2012, which claims the benefit of priority of U.S. Provisional Application No. 61/538,039, filed Sep. 22, 2011, all of which are incorporated herein by reference.

FIELD OF THE INVENTION

This invention is directed to the treatment of osteoporosis using N-(4-{[6,7-bis(methyloxy)quinolin-4-yl]oxy}phenyl)-N'-(4-fluorophenyl)cyclopropane-1,1-dicarboxamide.

BACKGROUND OF THE INVENTION

Osteoporosis is a disease characterized by low bone mass and micro-architectural deterioration of bone tissue leading to enhanced bone fragility and a consequent increase in fracture risk. The disease causes bones to become fragile and brittle and affects both men and women. Osteoporotic bones increase the risk of fracture after minimal trauma. Globally there are an estimated 35 million women and 14 million men with osteoporosis or low bone mass. In the United States, one in four adults over the age of 50 is likely to suffer from an osteoporotic fracture. Osteoporosis and the resultant fractures represent a huge public health burden, in part because the disease strikes silently—by the time a patient is diagnosed with an osteoporotic fracture, the damage to bones has already been done.

Bone continually undergoes a process called remodeling. Bone loss occurs in osteoporosis because the normal process of remodeling, or bone turnover, removes more bone than it replaces. Bone remodeling involves two distinct stages: bone resorption (breakdown) and bone formation. Calcium is stored in bone. When it is needed in the body, bone cells called osteoclasts attach to the bone surface and break it down, leaving cavities in the bone. Bone forming cells called osteoblasts then fill the cavities with an organic matrix called osteoid. The osteoid then spontaneously mineralizes with calcium phosphate to reform the hard bone. Osteoblasts that remain embedded in the matrix are called osteocytes.

During aging and as a result of other conditions that may lead to increased risk of losing bone mass such as during treatment for prostate or breast cancer or as the result of malnutrition, the rate of bone turnover increases in both genders, and at the tissue level, osteoblastic bone formation is slower than osteoclastic bone resorption due to the decreased number and activity of individual osteoblastic cells (Marie and Kassem, 2011). Bone resorption takes less time than bone formation. Bone resorption at a particular bone site takes about two weeks; formation takes three months or more. As a result, there is a shortfall of bone at what are called remodeling spaces. Normally, this is of little consequence, but if the remodeling cycle is out of balance, bone turnover can result in major bone loss. High bone turnover is believed to increase fracture risk.

As a result, a need remains for methods for treating osteoporosis.

SUMMARY OF THE INVENTION

These and other needs are met by the present invention which is directed to a method for treating osteoporosis. The method comprises administering a therapeutically effective amount of a compound to a patient in need of such treatment.

In one embodiment of this and other aspects, the compound is a compound of Formula I

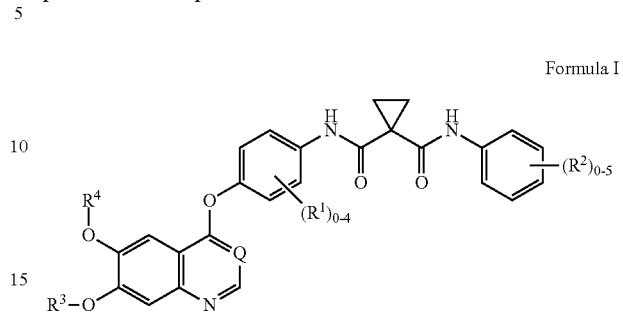

Formula I or a pharmaceutically acceptable salt thereof, wherein:
$R^1$ is halo;
$R^2$ is halo;
$R^3$ is $(C_1-C_6)$alkyl;
$R^4$ is $(C_1-C_6)$alkyl; and
Q is CH or N.

In another embodiment, the compound of Formula I is a compound of Formula Ia.

Formula Ia or a pharmaceutically acceptable salt thereof, wherein:
$R^1$ is halo;
$R^2$ is halo; and
Q is CH or N.

In another embodiment, the compound of Formula I is Compound 1:

Compound 1 or a pharmaceutically acceptable salt thereof. Compound 1 is known as N-(4-{[6,7-bis(methyloxy)quinolin-4-yl]oxy}phenyl)-N'-(4-fluorophenyl)cyclopropane-1,1-dicarboxamide and as cabozantinib.

In another embodiment, the compound of Formula I, Ia, or Compound 1 is administered as a pharmaceutical composition comprising a pharmaceutically acceptable additive, diluent, or excipient at a dosage sufficient to ameliorate the effects of abnormal bone turnover.

In another aspect, the invention provides a method for treating osteoporosis in patients with an increased risk of losing bone mass. Patients with an increased risk of losing bone mass include patients who are postmenopausal women and aging men, or who have or are currently undergoing treatment for cancer such as prostate or breast cancer or patients with malnutrition. The method comprises administering a therapeutically effective amount of a compound of Formula I, Ia, or Compound 1 to a patient in need of such treatment.

In another aspect, the invention provides a method for preventing osteoporosis, comprising administering a therapeutically effective amount of a compound of Formula I, Ia, or Compound 1 to a patient in need of such treatment.

In another aspect, the invention provides a method for increasing the bone mineral density of patient with osteoporosis, comprising administering a therapeutically effective amount of a compound of Formula I, Ia, or Compound 1 to a patient in need of such treatment.

In these and other aspects, the ability of the compound of Formula I to treat, ameliorate, or reduce the severity of osteoporosis can be determined both qualitatively and quantitatively using various circulating or urinary markers or various imaging technologies. Markers that may be useful for the individual monitoring of osteoporotic patients treated with antiresorptive agents include serum total alkaline phosphatase, serum bone-specific alkaline phosphatase, serum osteocalcin, serum C-terminal propeptide of type 1 procollagen C1NP or serum N-terminal propeptide of type I procollagen (P1NP) [to monitor bone formation], urinary hydroxyproline, urinary total pyridinoline (PYD), urinary free deoxypyridinoline (DPD), urinary cross-linked N-terminal telopeptides of type 1 collagen (NTx), urinary or serum cross-linked C-terminal telopeptides of type 1 collagen (CTx), bone sialoprotein (BSP), and tartrate-resistant acid phosphatase 5b (TRACP-5b) [to monitor bone resorption].

Imaging technologies that may be useful in assessing the ability of a compound of Formula I, Ia, or Compound 1 to treat, ameliorate, or reduce the severity of osteoporosis include magnetic resonance imaging, positron emission tomography, computed tomography (CT), and X-ray absorptometry.

In another aspect, the invention provides a prognostic method for osteoporosis in a subject, comprising:
  (a) measuring the level of P1NP, CTx or TRACP 5b in a sample from the subject;
  (b) comparing the level of P1NP, CTx or TRACP 5b measured in step (a) to a standard level of P1NP, CTx or TRACP 5b to determine if the sample from the subject has aberrant levels of P1NP, CTx or TRACP 5b;
  (c) selecting a treatment regimen with the Compound of Formula I, Ia, or 1 based on aberrant levels of P1NP, CTx or TRACP 5b or administering the Compound of Formula I, Ia, or 1 according to the treatment regimen such that the osteoporosis is inhibited in the subject.

In another aspect, the invention provides a method for stimulating osteoblast differentiation and/or activity in a patient in need of such treatment, comprising administering to the patient an effect amount of a Compound of Formula I, Ia, or Compound 1.

In another aspect, the invention provides a method for stimulating bone formation in a patient in need of such treatment, comprising administering to the patient an effect amount of a Compound of Formula I, Ia, or Compound 1.

In another aspect, the invention provides a method for inhibiting osteoclast differentiation in a patient in need of such treatment, comprising administering to the patient an effect amount of a Compound of Formula I, Ia, or Compound 1.

In another aspect, the invention provides a method for modulating bone turnover toward bone formation in a patient in need of such treatment, comprising administering to the patient an effect amount of a Compound of Formula I, Ia, or Compound 1.

In another aspect, the invention provides a method for treating osteoporosis in ovarectomized patients, comprising administering to the patient an effect amount of a Compound of Formula I, Ia, or Compound 1.

In another aspect, the invention provides a method for modulating bone turnover toward bone formation in ovarectomized patients, comprising administering to the patient an effect amount of a Compound of Formula I, Ia, or Compound 1.

BRIEF SUMMARY OF THE FIGURES

FIG. 6 depicts the design of a study of the short-term effects of Compound 1 on bone turnover markers in a rat ovariectomy (OVX model).

DETAILED DESCRIPTION OF THE INVENTION

Abbreviations and Definitions

Figure 1:
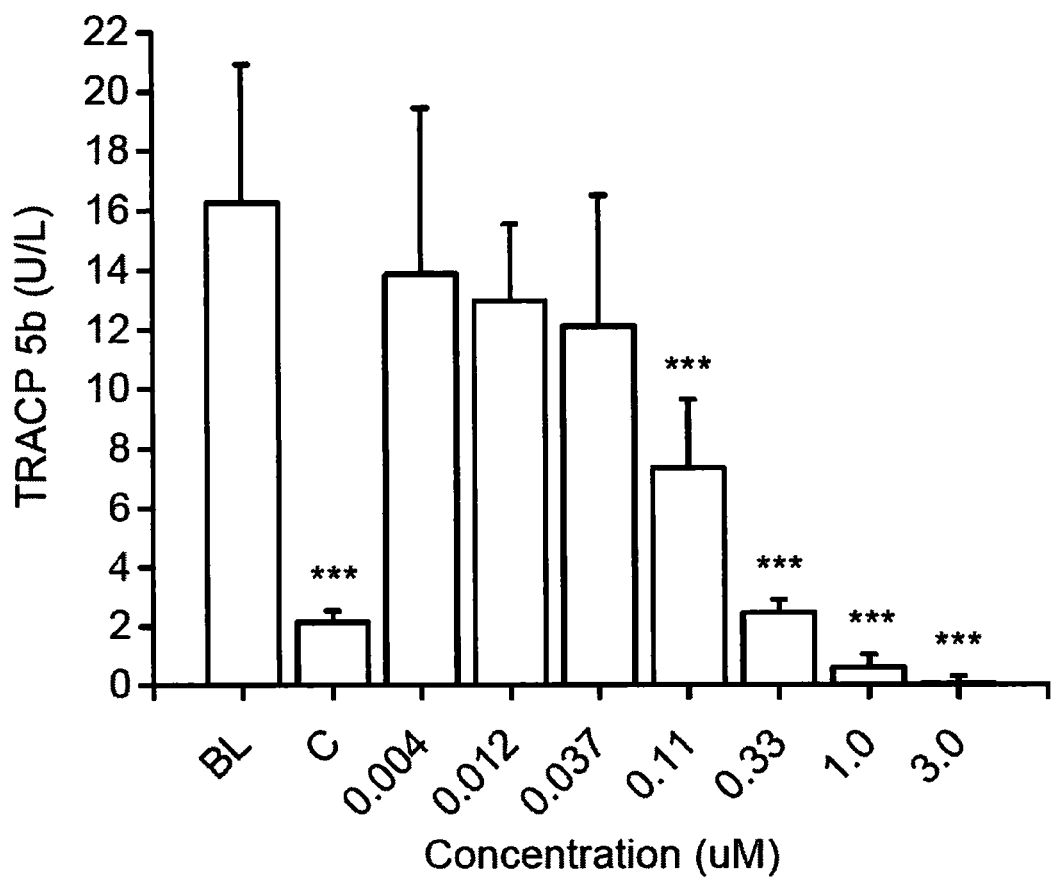
FIG. 1 depicts the effect of Compound 1 on osteoclast differentiation was measured at day 7 as TRACP 5b activity (U/L) secreted in the culture medium.

The following abbreviations and terms have the indicated meanings throughout:

| Abbreviation | Meaning |
| --- | --- |
| Ac | Acetyl |
| Br | Broad |
| ° C. | Degrees Celsius |
| c- | Cyclo |
| CBZ | CarboBenZoxy = benzyloxycarbonyl |
| d | Doublet |
| dd | Doublet of doublet |
| dt | Doublet of triplet |
| DCM | Dichloromethane |
| DME | 1,2-dimethoxyethane |
| DMF | N,N-Dimethylformamide |
| DMSO | dimethyl sulfoxide |
| Dppf | 1,1'-bis(diphenylphosphano)ferrocene |
| EI | Electron Impact ionization |
| G | Gram(s) |
| h or hr | Hour(s) |
| HPLC | High pressure liquid chromatography |
| L | Liter(s) |
| M | Molar or molarity |
| m | Multiplet |
| Mg | Milligram(s) |
| MHz | Megahertz (frequency) |

| Abbreviation | Meaning |
| --- | --- |
| Min | Minute(s) |
| mL | Milliliter(s) |
| µL | Microliter(s) |
| µM | Micromole(s) or micromolar |
| mM | Millimolar |
| Mmol | Millimole(s) |
| Mol | Mole(s) |
| MS | Mass spectral analysis |
| N | Normal or normality |
| nM | Nanomolar |
| NMR | Nuclear magnetic resonance spectroscopy |
| q | Quartet |
| RT | Room temperature |
| s | Singlet |
| t or tr | Triplet |
| TFA | Trifluoroacetic acid |
| THF | Tetrahydrofuran |
| TLC | Thin layer chromatography |

The symbol "—" means a single bond, "═" means a double bond.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

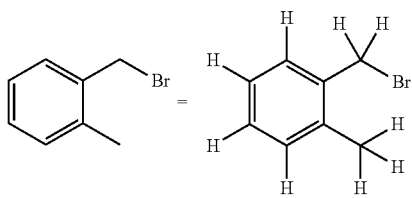

If a group "R" is depicted as "floating" on a ring system, as for example in the formula:

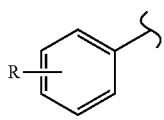

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

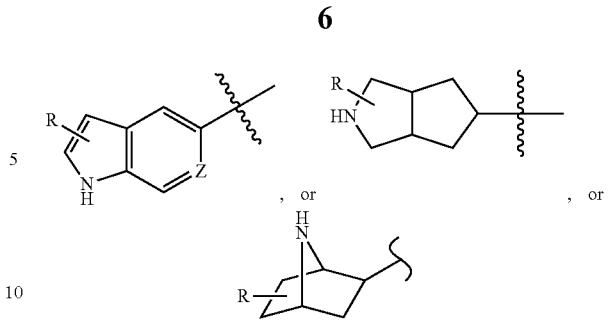

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "Z" equals ═CH—) from one of the ring atoms, so long as a stable structure is formed. In the example depicted, the "R" group may reside on either the 5-membered or the 6-membered ring of the fused ring system. When a group "R" is depicted as existing on a ring system containing saturated carbons, as for example in the formula:

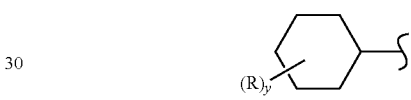

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

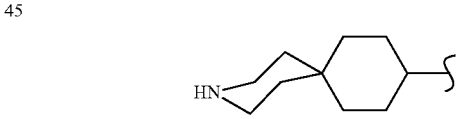

"Halogen" or "halo" refers to fluorine, chlorine, bromine or iodine.

"Yield" for each of the reactions described herein is expressed as a percentage of the theoretical yield.

"Patient" for the purposes of the present invention includes humans and other animals, particularly mammals, and other organisms. Thus the methods are applicable to both human therapy and veterinary applications. In another embodiment the patient is a mammal, and in another embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, malic acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Therapeutically effective amount" is an amount of a compound of the invention, that when administered to a patient, ameliorates a symptom of the disease. A therapeutically effective amount is intended to include an amount of a compound alone or in combination with other active ingredients effective to treat, ameliorate, or reduce the severity of osteoporosis. The amount of a compound of the invention which constitutes a "therapeutically effective amount" will vary depending on the compound, the disease state and its severity, the age of the patient to be treated, and the like. The therapeutically effective amount can be determined by one of ordinary skill in the art having regard to their knowledge and to this disclosure, but will generally be in the range of about 0.1 to 1,000 mg per day, and more specifically in the range of 1 to 100 mg per day.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experience.

Embodiments

In one embodiment the compound of Formula I is the compound of Formula Ia:

Formula Ia

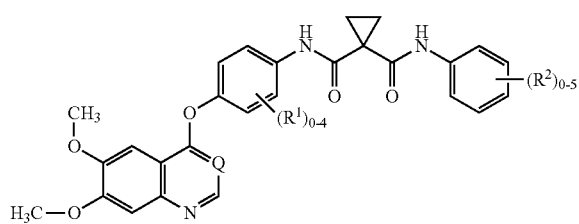

or a pharmaceutically acceptable salt thereof, wherein:
$R^1$ is halo;
$R^2$ is halo; and
Q is CH or N.

In another embodiment, the compound of Formula I is Compound 1:

Compound 1

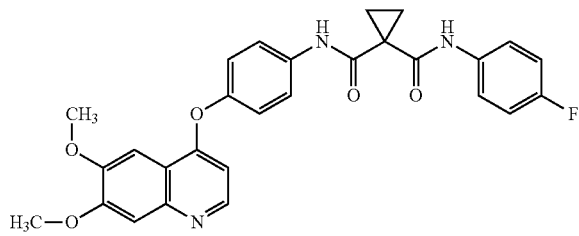

or a pharmaceutically acceptable salt thereof.

As indicated previously, Compound 1 is referred to herein as N-(4-{[6,7-bis(methyloxy)quinolin-4-yl]oxy}phenyl)-N'-(4-fluorophenyl)cyclopropane-1,1-dicarboxamide. WO 2005/030140 discloses Compound 1 and describes how it is made (Example 12, 37, 38, and 48) and also discloses the therapeutic activity of this compound to inhibit, regulate and/or modulate the signal transduction of kinases, (Assays, Table 4, entry 289). Example 48 is on paragraph [0353] in WO 2005/030140.

In other embodiments, the compound of Formula I, Ia, or Compound 1, or a pharmaceutically acceptable salt thereof, is administered as a pharmaceutical composition, wherein the pharmaceutical composition additionally comprises a pharmaceutically acceptable carrier, excipient, or diluent.

The compound of Formula I, Formula Ia and Compound 1, as described herein, includes both the recited compounds as well as individual isomers and mixtures of isomers. In each instance, the compound of Formula I includes the pharmaceutically acceptable salts, hydrates, and/or solvates of the recited compounds and any individual isomers or mixture of isomers thereof.

In other embodiments, the compound of Formula I, Ia, or Compound 1 can be the (L)-malate salt. The malate salt of the Compound of Formula I and of Compound 1 is disclosed in PCT/US2010/021194 and 61/325,095.

In other embodiments, the compound of Formula I can be the (D)-malate salt.

In other embodiments, the compound of Formula Ia can be malate salt.

In other embodiments, the compound of Formula Ia can be the (L)-malate salt.

In other embodiments, Compound 1 can be (D)-malate salt.

In other embodiments, Compound 1 can be the malate salt.

In other embodiments, Compound 1 can be the (D)-malate salt.

In another embodiment, the malate salt is in the crystalline N-1 form of the (L) malate salt and/or the (D) malate salt of the Compound 1 as disclosed in U.S. patent Application Ser. No. 61/325,095. Also see WO 2008/083319 for the properties of crystalline enantiomers, including the N-1 and/or the N-2 crystalline forms of the malate salt of Compound 1. Methods of making and characterizing such forms are fully described in PCT/US10/21194, which is incorporated herein by reference in its entirety.

In another embodiment, the invention is directed to a method for ameliorating the symptoms of osteoporosis, comprising administering to a patient in need of such treatment a therapeutically effective amount of a compound of Formula I in any of the embodiments disclosed herein.

In another embodiment, the invention is directed to a method for ameliorating the symptoms of osteoporosis, comprising administering to a patient in need of such treatment a compound of Formula I in any of the embodiments disclosed herein at a daily dose that is less than or equal to 100 mg. In a specific embodiment, the Compound of Formula I is Compound 1. In this and the following embodiments, the dose is a quantity that is greater than 0 mg.

In another embodiment, the invention is directed to a method for ameliorating the symptoms of osteoporosis, comprising administering to a patient in need of such treatment a compound of Formula I in any of the embodiments disclosed herein at a daily dose that is less than or equal to 90 mg. In a specific embodiment, the Compound of Formula I is Compound 1.

In another embodiment, the invention is directed to a method for ameliorating the symptoms of osteoporosis, comprising administering to a patient in need of such treatment a compound of Formula I in any of the embodiments disclosed herein at a daily dose that is less than or equal to 80 mg. In a specific embodiment, the Compound of Formula I is Compound 1.

In another embodiment, the invention is directed to a method for ameliorating the symptoms of osteoporosis, comprising administering to a patient in need of such treatment a compound of Formula I in any of the embodiments disclosed herein at a daily dose that is less than or equal to 70 mg. In a specific embodiment, the Compound of Formula I is Compound 1.

In another embodiment, the invention is directed to a method for ameliorating the symptoms of osteoporosis, comprising administering to a patient in need of such treatment a compound of Formula I in any of the embodiments disclosed herein at a daily dose that is less than or equal to 60 mg. In a specific embodiment, the Compound of Formula I is Compound 1.

In another embodiment, the invention is directed to a method for ameliorating the symptoms of osteoporosis, comprising administering to a patient in need of such treatment a compound of Formula I in any of the embodiments disclosed herein at a daily dose that is less than or equal to 50 mg. In a specific embodiment, the Compound of Formula I is Compound 1.

In another embodiment, the invention is directed to a method for ameliorating the symptoms of osteoporosis, comprising administering to a patient in need of such treatment a compound of Formula I in any of the embodiments disclosed herein at a daily dose that is less than or equal to 40 mg. In a specific embodiment, the Compound of Formula I is Compound 1.

In another embodiment, the invention is directed to a method for ameliorating the symptoms of osteoporosis, comprising administering to a patient in need of such treatment a compound of Formula I in any of the embodiments disclosed herein at a daily dose that is less than or equal to 30 mg. In a specific embodiment, the Compound of Formula I is Compound 1.

In another embodiment, the invention is directed to a method for ameliorating the symptoms of osteoporosis, comprising administering to a patient in need of such treatment a compound of Formula I in any of the embodiments disclosed herein at a daily dose that is less than or equal to 20 mg. In a specific embodiment, the Compound of Formula I is Compound 1.

In another embodiment, the invention is directed to a method for ameliorating the symptoms of osteoporosis, comprising administering to a patient in need of such treatment a compound of Formula I in any of the embodiments disclosed herein at a daily dose that is less than or equal to 10 mg. In a specific embodiment, the Compound of Formula I is Compound 1.

In another embodiment, the invention is directed to a method for ameliorating the symptoms of osteoporosis, comprising administering to a patient in need of such treatment a compound of Formula I in any of the embodiments disclosed herein at a daily dose that is less than or equal to 5 mg. In a specific embodiment, the Compound of Formula I is Compound 1.

In another embodiment, the invention is directed to a method for ameliorating the symptoms of osteoporosis, comprising administering to a patient in need of such treatment a compound of Formula I in any of the embodiments disclosed herein at a daily dose that is from 0.01 mg to 25 mg. In a specific embodiment, the Compound of Formula I is Compound 1.

In another embodiment, the invention is directed to a method for ameliorating the symptoms of osteoporosis, comprising administering to a patient in need of such treatment a compound of Formula I in any of the embodiments disclosed herein at a daily dose that is from 0.1 mg to 15 mg. In a specific embodiment, the Compound of Formula I is Compound 1.

In another embodiment, the invention is directed to a method for ameliorating the symptoms of osteoporosis, comprising administering to a patient in need of such treatment a compound of Formula I in any of the embodiments disclosed herein at a daily dose that is from 1 mg to 10 mg. In a specific embodiment, the Compound of Formula I is Compound 1.

In another embodiment, the invention is directed to a method for reducing the severity of osteoporosis in patients who have been treated or are undergoing treatment for breast cancer or prostate cancer comprising administering to a patient in need of such treatment a compound of Formula I in any of the embodiments disclosed herein at a daily dose that is less than or equal to 100, 95, 90, 85, 80, 75, 70, 65, 60, 55, 50, 45, 40, 35, 30, 25, 20, 15, 10, or 5 mg. In some embodiments, the cancer is breast cancer, prostate cancer, bone cancer and/or bone tumors. In a specific embodiment, the Compound of Formula I is Compound 1. In a specific embodiment, the Compound of Formula I is Compound 1 and the dose is from between 0.01 and 25 mg.

In another embodiment, the invention is directed to a method for ameliorating abnormal deposition of unstructured bone accompanied, increased skeletal fractures, spinal cord compression, and severe bone pain of osteoporosis, comprising administering to a patient in need of such treatment a therapeutically effective amount of a compound of Formula I in any of the embodiments disclosed herein at a daily dose that is less than or equal to 1100, 95, 90, 85, 80, 75, 70, 65, 60, 55, 50, 45, 40, 35, 30, 25, 20, 15, 10, or 5 mg. In a specific embodiment, the Compound of Formula I is Compound 1 and the dose is from between 0.01 and 25 mg.

As indicated previously, the ability of the compound of Formula I to treat, ameliorate, or reduce the severity of osteoporosis can be determined both qualitatively and quantitatively using various circulating or urinary markers. In some embodiments, the markers useful for the individual monitoring of osteoporotic patients treated with antiresorptive agents can be selected from serum total alkaline phosphatase, serum bone-specific alkaline phosphatase, serum osteocalcin, serum type 1 procollagen (C-terminal/N-terminal): C1NP or P1NP [to monitor bone formation], urinary hydroxyproline, urinary total pyridinoline (PYD), urinary free deoxypyridinoline (DPD), urinary cross-linked N-terminal telopeptides of type 1 collagen (NTx), urinary or serum cross-linked C-terminal telopeptides of type 1 collagen (CTx), bone sialoprotein (BSP), and tartrate-resistant acid phosphatase 5b [to monitor bone resorption].

In a particular embodiment, the marker is CTx. CTx is the portion of type 1 collagen that is cleaved by osteoclasts during bone resorption, and its serum levels are therefore considered to be proportional to osteoclastic activity at the time the blood sample is drawn. Consequently, serum CTx is widely used to monitor the effects of bisphosphonates on bone (Marx et al, 2007). The bone turnover substudy of the Fracture REduction Evaluation of Denosumab in Osteoporosis every 6 Months (FREEDOM) Trial included 160 women randomized to subcutaneous denosumab (60 mg) or placebo injections every 6 months for 3 years. One month after injection, serum CTx levels in all denosumab-treated subjects decreased to levels below the premenopausal reference interval. Moreover, there was a significant correlation between CTx reduction and increased bone mineral density in denosumab-treated subjects (Eastell et al, 2011). In addition to these effects on CTx, in a Phase 1 study, one subcutaneous injection of denosumab suppressed urinary NTx in a dose-dependent manner by up to 81% in postmenopausal women for as long as 6 months (Bekker et al, 2004).

In another embodiment, the marker is TRACP-5b

In patients with metastatic castration resistant prostate cancer, administration of Compound 1 was associated with a decrease in plasma CTx regardless of whether subjects were previously treated with bisphosphonates (Hussain et al, 2011). Similar effects with Compound 1 were observed in patients with no known bone metastases (Gordon et al, 2011), where prior bisphosphonate use was presumably for treating patients with osteoporosis. The ability of Compound 1 to reduce plasma CTx levels in patients regardless of prior bisphosphonate treatment and regardless of the presence of metastatic bone lesions suggests a powerful effect on blocking abnormal bone turnover.

Thus, in another embodiment, the invention is directed to a method of decreasing plasma CTx in a patient suffering from osteoporosis, comprising administering to a patient in need of such treatment a compound of Formula I in any of the embodiments disclosed herein at a daily dose that is less than or equal to 100, 95, 90, 85, 80, 75, 70, 65, 60, 55, 50, 45, 40, 35, 30, 25, 20, 15, 10, or 5 mg once daily. In a specific embodiment, the Compound of Formula I is Compound 1 and the dose is from between 0.01 and 25 mg.

In another aspect, the invention provides a prognostic method for osteoporosis in a subject, comprising:
  (a) measuring the level of P1NP, CTx or TRACP 5b in a sample form the subject;
  (b) comparing the level of P1NP, CTx or TRACP 5b measured in step (a) to a standard level of P1NP, CTx or TRACP 5b b to determine if the sample from the subject has aberrant levels of P1NP, CTx or TRACP 5b;
  (c) selecting a treatment regimen with the Compound of Formula I, Ia, or 1 based on aberrant levels of P1NP, CTx or TRACP 5b or administering the Compound of Formula I, Ia, or 1 according to the treatment regimen such that the osteoporosis is inhibited in the subject.

In another embodiment, the invention provides a method for stimulating osteoblast differentiation and/or activity in a patient in need of such treatment, comprising administering to the patient an effect amount of a Compound of Formula I, Ia, or Compound 1 in any of the embodiments disclosed herein at a daily dose that is less than or equal to 100, 95, 90, 85, 80, 75, 70, 65, 60, 55, 50, 45, 40, 35, 30, 25, 20, 15, 10, or 5 mg once daily. In a specific embodiment, the Compound of Formula I is Compound 1 and the dose is from between 0.01 and 25 mg once daily.

In another aspect, the invention provides a method for stimulating bone formation in a patient in need of such treatment, comprising administering to the patient an effect amount of a Compound of Formula I, Ia, or Compound 1 in any of the embodiments disclosed herein at a daily dose that is less than or equal to 100, 95, 90, 85, 80, 75, 70, 65, 60, 55, 50, 45, 40, 35, 30, 25, 20, 15, 10, or 5 mg once daily. In a specific embodiment, the Compound of Formula I is Compound 1 and the dose is from between 0.01 and 25 mg once daily.

In another aspect, the invention provides a method for inhibiting osteoclast differentiation in a patient in need of such treatment, comprising administering to the patient an effect amount of a Compound of Formula I, Ia, or Compound 1 in any of the embodiments disclosed herein at a daily dose that is less than or equal to 100, 95, 90, 85, 80, 75, 70, 65, 60, 55, 50, 45, 40, 35, 30, 25, 20, 15, 10, or 5 mg once daily. In a specific embodiment, the Compound of Formula I is Compound 1 and the dose is from between 0.01 and 25 mg once daily.

In another aspect, the invention provides a method for modulating bone turnover toward bone formation in a patient in need of such treatment, comprising administering to the patient an effect amount of a Compound of Formula I, Ia, or Compound 1 in any of the embodiments disclosed herein at a daily dose that is less than or equal to 100, 95, 90, 85, 80, 75, 70, 65, 60, 55, 50, 45, 40, 35, 30, 25, 20, 15, 10, or 5 mg once daily. In a specific embodiment, the Compound of Formula I is Compound 1 and the dose is from between 0.01 and 25 mg once daily.

In another aspect, the invention provides a method for treating osteoporosis in ovarectomized patients, comprising administering to the patient an effect amount of a Compound of Formula I, Ia, or Compound 1 in any of the embodiments disclosed herein at a daily dose that is less than or equal to 100, 95, 90, 85, 80, 75, 70, 65, 60, 55, 50, 45, 40, 35, 30, 25, 20, 15, 10, or 5 mg once daily. In a specific embodiment, the Compound of Formula I is Compound 1 and the dose is from between 0.01 and 25 mg once daily.

In another aspect, the invention provides a method for modulating bone turnover toward bone formation in ovarectomized patients, comprising administering to the patient an effect amount of a Compound of Formula I, Ia, or Compound 1 in any of the embodiments disclosed herein at a daily dose that is less than or equal to 100, 95, 90, 85, 80, 75, 70, 65, 60, 55, 50, 45, 40, 35, 30, 25, 20, 15, 10, or 5 mg once daily. In a specific embodiment, the Compound of Formula I is Compound 1 and the dose is from between 0.01 and 25 mg once daily.

In another embodiment, the invention provides a method for treating osteoporosis in a patient comprising administering to the patient an effect amount of a Compound of Formula I, Ia, or Compound 1 in any of the embodiments disclosed herein at a daily dose that is less than or equal to 100, 95, 90, 85, 80, 75, 70, 65, 60, 55, 50, 45, 40, 35, 30, 25, 20, 15, 10, or 5 mg once daily. In one embodiment, the treatment results stimulating osteoblast differentiation. In another embodiment, the treatment results in stimulating bone formation. In another embodiment, the treatment results in the inhibition of osteoclast differentiation and/or activity. In another embodiment, the treatment results in a modulation of turnover toward bone formation. In these and other embodiments, the Compound of Formula I is Compound 1 and the dose is from between 0.01 and 25 mg once daily.

Administration

Administration of the compound of Formula I, Formula Ia, or Compound 1, or a pharmaceutically acceptable salt thereof, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin dosages (which can be in capsules or tablets), powders, solutions, suspensions, or aerosols, or the like, specifically in unit dosage forms suitable for simple administration of precise dosages.

The compositions will include a conventional pharmaceutical carrier or excipient and a compound of Formula I as the/an active agent, and, in addition, may include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the compound of Formula I may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The choice of composition depends on various factors such as the mode of drug administration (e.g., for oral administration, compositions in the form of tablets, pills or capsules) and the bioavailability of the drug substance. Recently, pharmaceutical compositions have been developed especially for drugs that show poor bioavailability based upon the principle that bioavailability can be increased by increasing the surface area i.e., decreasing particle size. For example, U.S. Pat. No. 4,107,288 describes a pharmaceutical composition having particles in the size range from 10 to 1,000 nm in which the active material is supported on a crosslinked matrix of macromolecules. U.S. Pat. No. 5,145,684 describes the production of a pharmaceutical composition in which the drug substance is pulverized to nanoparticles (average particle size of 400 nm) in the presence of a surface modifier and then dispersed in a liquid medium to give a pharmaceutical composition that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the compound of Formula I, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administration are, for example, suppositories that can be prepared by mixing the compound of Formula I with, for example, suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of the compound of Formula I include ointments, powders, sprays, and inhalants. The active component is admixed under sterile conditions with a physiologically acceptable carrier and any preservatives, buffers, or propellants as may be required. Ophthalmic compositions, eye ointments, powders, and solutions are also contemplated as being within the scope of this disclosure.

Compressed gases may be used to disperse the compound of Formula I in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of Formula I, or a pharmaceutically acceptable salt thereof, and 99% to 1% by weight of a suitable pharmaceutical excipient. In one example, the composition will be between about 5% and about 75% by weight of a compound(s) of Formula I, Formula Ia, or Compound 1, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of Formula I, or a pharmaceutically acceptable salt thereof, for treatment of a disease-state in accordance with the teachings of this disclosure.

The compounds of this disclosure, or their pharmaceutically acceptable salts or solvates, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compound of Formula I, Formula Ia, or Compound 1, can be administered to a patient at dosage levels in the range of about 0.1 to about 1,000 mg per day, and from about 1 to about 150 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

In other embodiments, the compound of Formula I, Formula Ia, or Compound 1, can be administered to the patient concurrently with other cancer treatments. Such treatments include other cancer chemotherapeutics, hormone replacement therapy, radiation therapy, or immunotherapy, among others. The choice of other therapy will depend on a number of factors including the metabolic stability and length of action of the compound, the age, body weight, general health, sex, diet, mode and time of administration, rate of excretion, drug combination, the severity of the particular disease-states, and the host undergoing therapy.

In one embodiment, the compound of Formula I, Formula Ia, or Compound 1 is administered orally as a capsule. In another embodiment, Compound 1 is administered orally as a capsule. The capsule may contain 100, 95, 90, 85, 80, 75, 70, 65, 60, 55, 50, 45, 40, 35, 30, 25, 20, 15, 10, or 5 mg or less of Compound 1. In one embodiment, the dose is from between 0.01 and 25 mg.

In another embodiment, the compound of Formula I, Formula Ia, or Compound 1 is administered orally as a tablet.

In another embodiment, Compound 1 or pharmaceutically acceptable salt of Compound 1 is administered orally as a tablet as provided in the following table.

| Ingredient | (% w/w) |
| --- | --- |
| Compound 1 | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00 |

In another embodiment, Compound 1 or pharmaceutically acceptable salt of Compound 1 is administered orally as a tablet as provided in the following table.

| Ingredient | (% w/w) |
|---|---|
| Compound 1 | 25.0-33.3 |
| Microcrystalline Cellulose | q.s |
| Hydroxypropyl Cellulose | 3 |
| Poloxamer | 0-3 |
| Croscarmellose Sodium | 6.0 |
| Colloidal Silicon Dioxide | 0.5 |
| Magnesium Stearate | 0.5-1.0 |
| Total | 100 |

In another embodiment, Compound 1 or pharmaceutically acceptable salt of Compound 1 is administered orally as a tablet as provided in the following table.

| Ingredient | Theoretical Quantity (mg/unit dose) |
|---|---|
| Compound 1 | 100.0 |
| Microcrystalline Cellulose PH-102 | 155.4 |
| Lactose Anhydrous 60M | 77.7 |
| Hydroxypropyl Cellulose, EXF | 12.0 |
| Croscarmellose Sodium | 24 |
| Colloidal Silicon Dioxide | 1.2 |
| Magnesium Stearate (Non-Bovine) | 3.0 |
| Opadry Yellow | 16.0 |
| Total | 416 |

The tablet formulations described above may be adapted to provide an oral dose of 95, 90, 85, 80, 75, 70, 65, 60, 55, 50, 45, 40, 35, 30, 25, 20, 15, 10, or 5 mg or less of Compound 1 or pharmaceutically acceptable salt of Compound 1. In one embodiment, the dose is from between 0.01 and 25 mg.

Preparation of Compound 1

Preparation of N-(4-{[6,7-bis(methyloxy)quinolin-4-yl]oxy}phenyl)-N'-(4-fluorophenyl)cyclopropane-1,1-dicarboxamide and the (L)-malate salt thereof.

The synthetic route used for the preparation of N-(4-[6,7-bis(methyloxy)quinolin-4-yl]oxy}phenyl)-N'-(4-fluorophenyl)cyclopropane-1,1-dicarboxamide and the (L)-malate salt thereof is depicted in Scheme 1:

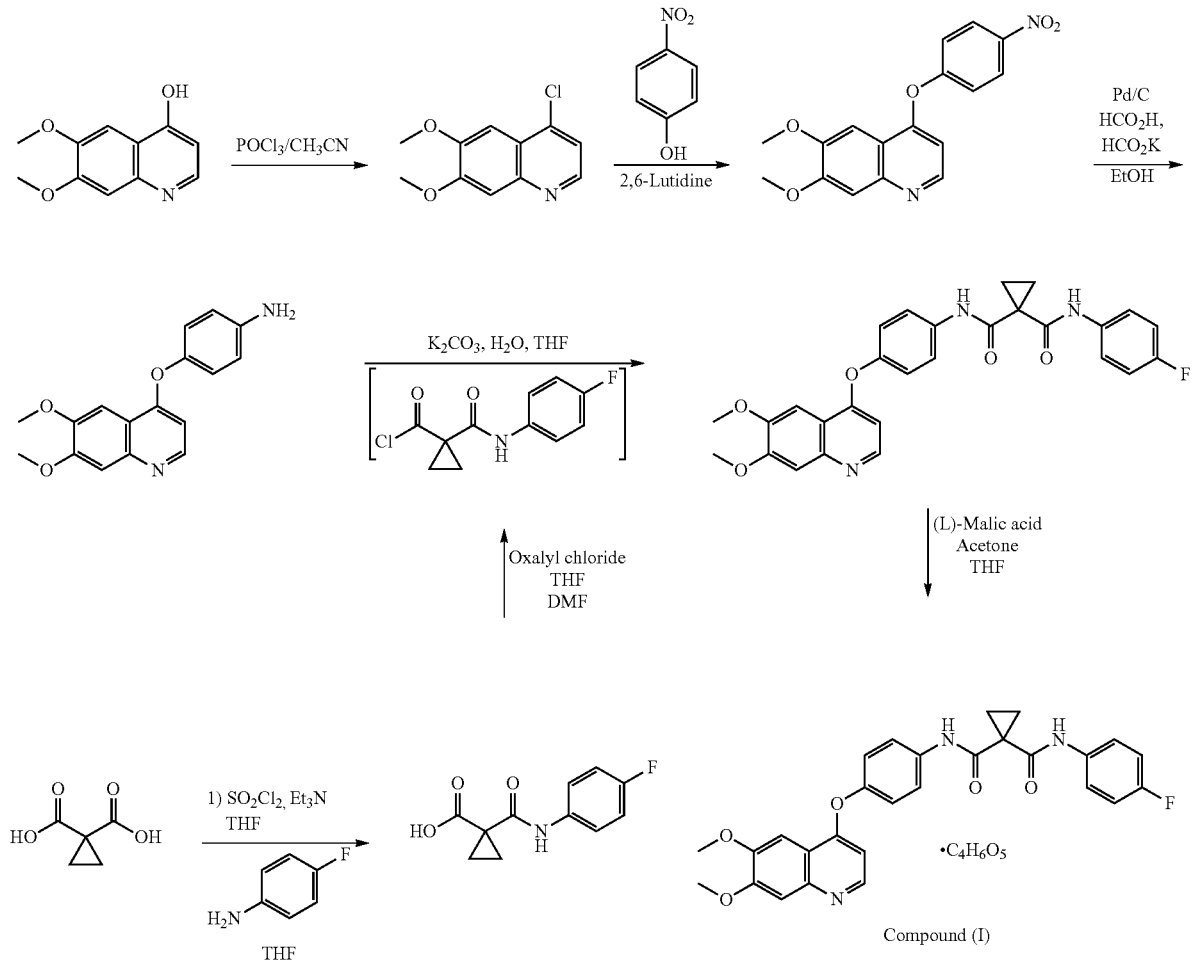

Preparation of 4-Chloro-6,7-dimethoxy-quinoline

A reactor was charged sequentially with 6,7-dimethoxy-quinoline-4-ol (10.0 kg) and acetonitrile (64.0 L). The resulting mixture was heated to approximately 65° C. and phosphorus oxychloride (POCl$_3$, 50.0 kg) was added. After the addition of POCl$_3$, the temperature of the reaction mixture was raised to approximately 80° C. The reaction was deemed complete (approximately 9.0 hours) when less than 2 percent of the starting material remained (in process high-performance liquid chromotography [HPLC] analysis). The reaction mixture was cooled to approximately 10° C. and then quenched into a chilled solution of dichloromethane (DCM, 238.0 kg), 30% NH$_4$OH (135.0 kg), and ice (440.0 kg). The resulting mixture was warmed to approximately 14° C., and phases were separated. The organic phase was washed with water (40.0 kg) and concentrated by vacuum distillation to remove the solvent (approximately 190.0 kg). Methyl-t-butyl ether (MTBE, 50.0 kg) was added to the batch, and the mixture was cooled to approximately 10° C., during which time the product crystallized out. The solids were recovered by centrifugation, washed with n heptane (20.0 kg), and dried at approximately 40° C. to afford the title compound (8.0 kg).

Preparation of 6,7-Dimethyl-4-(4 nitro-phenoxy)-quinoline

A reactor was sequentially charged with 4-chloro-6,7-dimethoxy-quinoline (8.0 kg), 4 nitrophenol (7.0 kg), 4 dimethylaminopyridine (0.9 kg), and 2,6 lutidine (40.0 kg). The reactor contents were heated to approximately 147° C. When the reaction was complete (less than 5 percent starting material remaining as determined by in process HPLC analysis, approximately 20 hours), the reactor contents were allowed to cool to approximately 25° C. Methanol (26.0 kg) was added, followed by potassium carbonate (3.0 kg) dissolved in water (50.0 kg). The reactor contents were stirred for approximately 2 hours. The resulting solid precipitate was filtered, washed with water (67.0 kg), and dried at 25° C. for approximately 12 hours to afford the title compound (4.0 kg).

Preparation of 4-(6,7-Dimethoxy-quinoline-4-yloxy)-phenylamine

A solution containing potassium formate (5.0 kg), formic acid (3.0 kg), and water (16.0 kg) was added to a mixture of 6,7-dimethoxy-4-(4-nitro-phenoxy)-quinoline (4.0 kg), 10 percent palladium on carbon (50 percent water wet, 0.4 kg) in tetrahydrofuran (THF, 40.0 kg) that had been heated to approximately 60° C. The addition was carried out such that the temperature of the reaction mixture remained approximately 60° C. When the reaction was deemed complete as determined using in-process HPLC analysis (less than 2 percent starting material remaining, typically 15 hours), the reactor contents were filtered. The filtrate was concentrated by vacuum distillation at approximately 35° C. to half of its original volume, which resulted in the precipitation of the product. The product was recovered by filtration, washed with water (12.0 kg), and dried under vacuum at approximately 50° C. to afford the title compound (3.0 kg; 97 percent area under curve (AUC)).

Preparation of 1-(4-Fluoro-phenylcarbamoyl)-cyclopropanecarboxylic acid

Triethylamine (8.0 kg) was added to a cooled (approximately 4° C.) solution of commercially available cyclopropane-1,1-dicarboxylic acid (21, 10.0 kg) in THF (63.0 kg) at a rate such that the batch temperature did not exceed 10° C. The solution was stirred for approximately 30 minutes, and then thionyl chloride (9.0 kg) was added, keeping the batch temperature below 10° C. When the addition was complete, a solution of 4-fluoroaniline (9.0 kg) in THF (25.0 kg) was added at a rate such that the batch temperature did not exceed 10° C. The mixture was stirred for approximately 4 hours and then diluted with isopropyl acetate (87.0 kg). This solution was washed sequentially with aqueous sodium hydroxide (2.0 kg dissolved in 50.0 L of water), water (40.0 L), and aqueous sodium chloride (10.0 kg dissolved in 40.0 L of water). The organic solution was concentrated by vacuum distillation followed by the addition of heptane, which resulted in the precipitation of solid. The solid was recovered by centrifugation and then dried at approximately 35° C. under vacuum to afford the title compound. (10.0 kg).

Preparation of 1-(4-Fluoro-phenylcarbamoyl)-cyclopropanecarbonyl chloride

Oxalyl chloride (1.0 kg) was added to a solution of 1-(4-fluoro-phenylcarbamoyl)-cyclopropanecarboxylic acid (2.0 kg) in a mixture of THF (11 kg) and N,N-dimethylformamide (DMF; 0.02 kg) at a rate such that the batch temperature did not exceed 30° C. This solution was used in the next step without further processing.

Preparation of N-(4-{[6,7-bis(methyloxy)quinolin-4-yl]oxy}phenyl)-N'-(4-fluorophenyl)cyclopropane-1,1-dicarboxamide The solution from the previous step containing 1-(4-fluoro-phenylcarbamoyl)-cyclopropanecarbonyl chloride was added to a mixture of 4-(6,7-dimethoxy-quinoline-4-yloxy)-phenylamine (3.0 kg) and potassium carbonate (4.0 kg) in THF (27.0 kg) and water (13.0 kg) at a rate such that the batch temperature did not exceed 30° C. When the reaction was complete (in typically 10 minutes), water (74.0 kg) was added. The mixture was stirred at 15-30° C. for approximately 10 hours, which resulted in the precipitation of the product. The product was recovered by filtration, washed with a pre-made solution of THF (11.0 kg) and water (24.0 kg), and dried at approximately 65° C. under vacuum for approximately 12 hours to afford the title compound (free base, 5.0 kg). $^1$H NMR (400 MHz, d$_6$-DMSO): δ 10.2 (s, 1H), 10.05 (s, 1H), 8.4 (s, 1H), 7.8 (m, 2H), 7.65 (m, 2H), 7.5 (s, 1H), 7.35 (s, 1H), 7.25 (m, 2H), 7.15 (m, 2H), 6.4 (s, 1H), 4.0 (d, 6H), 1.5 (s, 4H). LC/MS: M+H=502.

Preparation of N-(4-{[6,7-bis(methyloxy)quinolin-4-yl]oxy}phenyl)-N'-(4-fluorophenyl)cyclopropane-1,1-dicarboxamide, (L) malate salt A solution of L-malic acid (2.0 kg) in water (2.0 kg) was added to a solution of Cyclopropane-1,1-dicarboxylic acid [4-(6,7-dimethoxy-quinoline-4-yloxy)-phenyl]-amide (4-fluoro-phenyl)-amide free base (15, 5.0 kg) in ethanol, maintaining a batch temperature of approximately 25° C. Carbon (0.5 kg) and thiol silica (0.1 kg) were then added, and the resulting mixture was heated to approximately 78° C., at which point water (6.0 kg) was added. The reaction mixture was then filtered, followed by the addition of isopropanol (38.0 kg), and was allowed to cool to approximately 25° C. The product was recovered by filtration and washed with isopropanol (20.0 kg), and dried at approximately 65° C. to afford the title compound (5.0 kg).

Alternative Preparation of N-(4-{[6,7-Bis(methyloxy)quinolin-4-yl]oxy}phenyl)-N'-(4-fluorophenyl)cyclopropane-1,1-dicarboxamide and the (L)-malate salt Thereof An alternative synthetic route that can be used for the preparation of N-(4-{[6,7-bis(methyloxy)quinolin-4-yl]oxy}phenyl)-N'-(4-fluorophenyl)cyclopropane-1,1-dicarboxamide and the (L)-malate salt thereof is depicted in Scheme 2.

Scheme 2
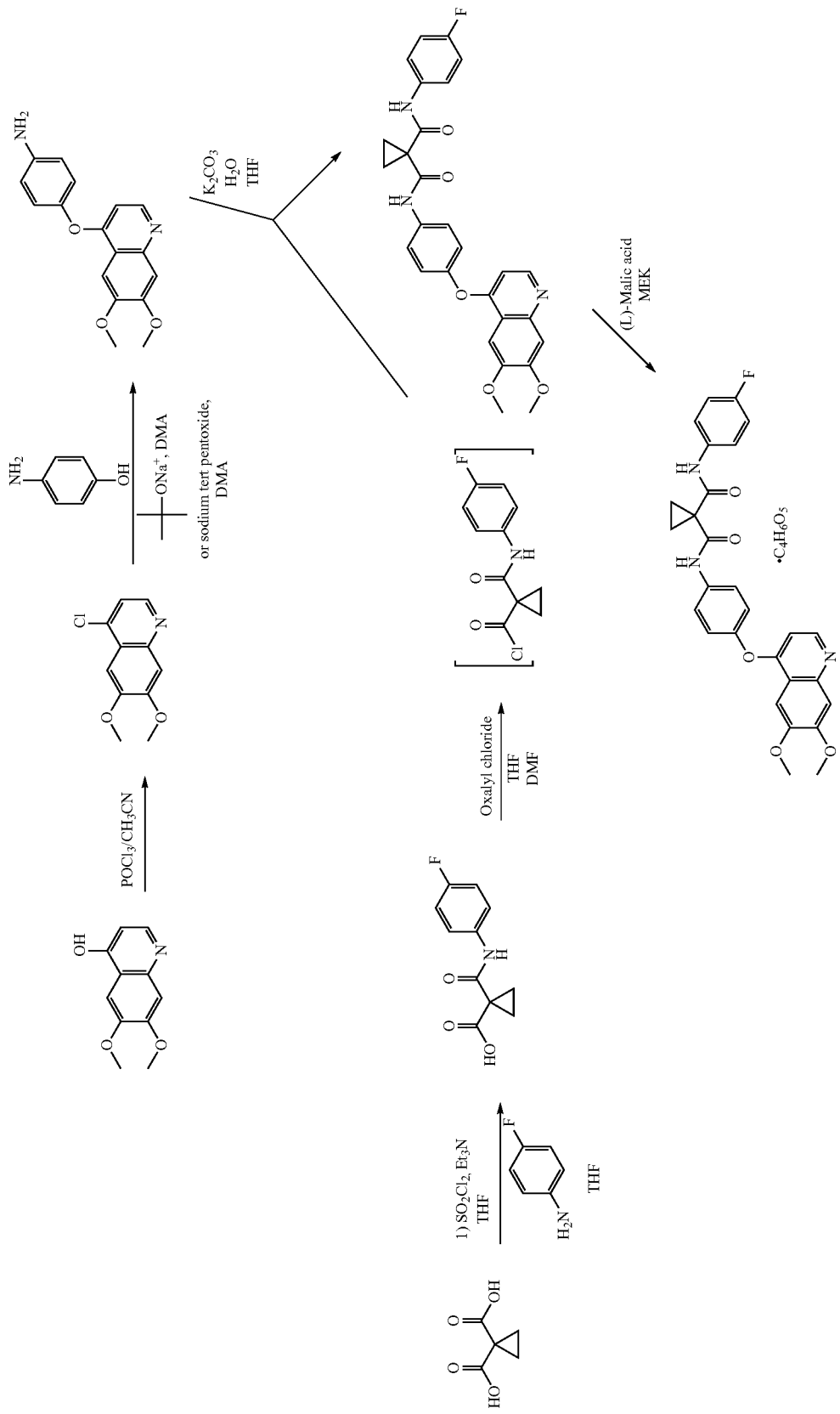

Preparation of 4-Chloro-6,7-dimethoxy-quinoline

A reactor was charged sequentially with 6,7-dimethoxy-quinoline-4-ol (47.0 kg) and acetonitrile (318.8 kg). The resulting mixture was heated to approximately 60° C. and phosphorus oxychloride (POCl$_3$, 130.6 kg) was added. After the addition of POCl$_3$, the temperature of the reaction mixture was raised to approximately 77° C. The reaction was deemed complete (approximately 13 hours) when less than 3% of the starting material remained (in-process high-performance liquid chromatography [HPLC] analysis). The reaction mixture was cooled to approximately 2-7° C. and then quenched into a chilled solution of dichloromethane (DCM, 482.8 kg), 26 percent NH$_4$OH (251.3 kg), and water (900 L). The resulting mixture was warmed to approximately 20-25° C., and phases were separated. The organic phase was filtered through a bed of AW hyflo super-cel NF (Celite; 5.4 kg) and the filter bed was washed with DCM (118.9 kg). The combined organic phase was washed with brine (282.9 kg) and mixed with water (120 L). The phases were separated and the organic phase was concentrated by vacuum distillation with the removal of solvent (approximately 95 L residual volume). DCM (686.5 kg) was charged to the reactor containing organic phase and concentrated by vacuum distillation with the removal of solvent (approximately 90 L residual volume). Methyl t-butyl ether (MTBE, 226.0 kg) was then charged and the temperature of the mixture was adjusted to −20 to −25° C. and held for 2.5 hours resulting in solid precipitate which was then filtered and washed with n-heptane (92.0 kg), and dried on a filter at approximately 25° C. under nitrogen to afford the title compound. (35.6 kg).

Preparation of 4-(6, 7-Dimethoxy-quinoline-4-yloxy)-phenylamine

4-Aminophenol (24.4 kg) dissolved in N,N-dimethylacetamide (DMA, 184.3 kg) was charged to a reactor containing 4-chloro-6,7-dimethoxyquinoline (35.3 kg), sodium t-butoxide (21.4 kg) and DMA (167.2 kg) at 20-25° C. This mixture was then heated to 100-105° C. for approximately 13 hours. After the reaction was deemed complete as determined using in-process HPLC analysis (less than 2 percent starting material remaining), the reactor contents were cooled at 15-20° C. and water (pre-cooled, 2-7° C., 587 L) charged at a rate to maintain 15-30° C. temperature. The resulting solid precipitate was filtered, washed with a mixture of water (47 L) and DMA (89.1 kg) and finally with water (214 L). The filter cake was then dried at approximately 25° C. on filter to yield crude 4-(6,7-dimethoxy-quinoline-4-yloxy)-phenylamine (59.4 kg wet, 41.6 kg dry calculated based on LOD). Crude 4-(6, 7-dimethoxy-quinoline-4-yloxy)-phenylamine was refluxed (approximately 75° C.) in a mixture of tetrahydrofuran (THF, 211.4 kg) and DMA (108.8 kg) for approximately 1 hour and then cooled to 0-5° C. and aged for approximately 1 hour after which time the solid was filtered, washed with THF (147.6 kg) and dried on a filter under vacuum at approximately 25° C. to yield 4-(6,7-dimethoxy-quinoline-4-yloxy)-phenylamine (34.0 kg).

Alternative Preparation of 4-(6,7-Dimethoxy-quinoline-4-yloxy)-phenylamine 4-chloro-6,7-dimethoxyquinoline (34.8 kg) and 4-aminophenol (30.8 kg) and sodium tert pentoxide (1.8 equivalents) 88.7 kg, 35 weight percent in THF) were charged to a reactor, followed by N,N-dimethylacetamide (DMA, 293.3 kg). This mixture was then heated to 105-115° C. for approximately 9 hours. After the reaction was deemed complete as determined using in-process HPLC analysis (less than 2 percent starting material remaining), the reactor contents were cooled at 15-25° C. and water (315 kg) was added over a two hour period while maintaining the temperature between 20-30° C. The reaction mixture was then agitated for an additional hour at 20-25° C. The crude product was collected by filtration and washed with a mixture of 88 kg water and 82.1 kg DMA, followed by 175 kg water. The product was dried on a filter drier for 53 hours. The LOD showed less than 1 percent w/w.

In an alternative procedure, 1.6 equivalents of sodium tert-pentoxide were used and the reaction temperature was increased from 110-120° C. In addition, the cool down temperature was increased to 35-40° C. and the starting temperature of the water addition was adjusted to 35-40° C., with an allowed exotherm to 45° C.

Preparation of 1-(4-Fluoro-phenylcarbamoyl)-cyclopropanecarboxylic acid

Triethylamine (19.5 kg) was added to a cooled (approximately 5° C.) solution of cyclopropane-1,1-dicarboxylic acid (24.7 kg) in THF (89.6 kg) at a rate such that the batch temperature did not exceed 5° C. The solution was stirred for approximately 1.3 hours, and then thionyl chloride (23.1 kg) was added, keeping the batch temperature below 10° C. When the addition was complete, the solution was stirred for approximately 4 hours keeping temperature below 10° C. A solution of 4-fluoroaniline (18.0 kg) in THF (33.1 kg) was then added at a rate such that the batch temperature did not exceed 10° C. The mixture was stirred for approximately 10 hours after which the reaction was deemed complete. The reaction mixture was then diluted with isopropyl acetate (218.1 kg). This solution was washed sequentially with aqueous sodium hydroxide (10.4 kg, 50 percent dissolved in 119 L of water) further diluted with water (415 L), then with water (100 L) and finally with aqueous sodium chloride (20.0 kg dissolved in 100 L of water). The organic solution was concentrated by vacuum distillation (100 L residual volume) below 40° C. followed by the addition of n-heptane (171.4 kg), which resulted in the precipitation of solid. The solid was recovered by filtration and washed with n-heptane (102.4 kg), resulting in wet, crude 1-(4-fluoro-phenylcarbamoyl)-cyclopropanecarboxylic acid (29.0 kg). The crude, 1-(4-fluoro-phenylcarbamoyl)-cyclopropanecarboxylic acid was dissolved in methanol (139.7 kg) at approximately 25° C. followed by the addition of water (320 L) resulting in slurry which was recovered by filtration, washed sequentially with water (20 L) and n-heptane (103.1 kg) and then dried on the filter at approximately 25° C. under nitrogen to afford the title compound (25.4 kg).

Preparation of 1-(4-Fluoro-phenylcarbamoyl)-cyclopropanecarbonyl chloride

Oxalyl chloride (12.6 kg) was added to a solution of 1-(4-fluoro-phenylcarbamoyl)-cyclopropanecarboxylic acid (22.8 kg) in a mixture of THF (96.1 kg) and N,N-dimethylformamide (DMF; 0.23 kg) at a rate such that the batch temperature did not exceed 25° C. This solution was used in the next step without further processing.

Alternative Preparation of 1-(4-Fluoro-phenylcarbamoyl)-cyclopropanecarbonyl chloride A reactor was charged with 1-(4-fluoro-phenylcarbamoyl)-cyclopropanecarboxylic acid (35 kg), 344 g DMF, and 175 kg THF. The reaction mixture was adjusted to 12-17° C. and then to the reaction mixture was charged 19.9 kg of oxalyl chloride over a period of 1 hour. The reaction mixture was left stirring at 12-17° C. for 3 to 8 hours. This solution was used in the next step without further processing.

Preparation of cyclopropane-1,1-dicarboxylic acid [4-(6,7-dimethoxy-quinoline-4-yloxy)-phenyl]-amide (4-fluoro-phenyl)-amide The solution from the previous step containing 1-(4-fluoro-phenylcarbamoyl)-cyclopropanecarbonyl chloride was added to a mixture of compound 4-(6,7-dimethoxy-quinoline-4-yloxy)-phenylamine (23.5 kg) and potassium carbonate (31.9 kg) in THF (245.7 kg) and water (116 L) at a rate such that the batch temperature did not exceed 30° C. When the reaction was complete (in approximately 20 minutes), water (653 L) was added. The mixture was stirred at 20-25° C. for approximately 10 hours, which resulted in the precipitation of the product. The product was recovered by filtration, washed with a pre-made solution of THF (68.6 kg) and water (256 L), and dried first on a filter under nitrogen at approximately 25° C. and then at approximately 45° C. under vacuum to afford the title compound (41.0 kg, 38.1 kg, calculated based on LOD).

Alternative Preparation of cyclopropane-1,1-dicarboxylic acid [4-(6,7-dimethoxy-quinoline-4-yloxy)-phenyl]-amide (4-fluoro-phenyl)-amide A reactor was charged with 4-(6,7-dimethoxy-quinoline-4-yloxy)-phenylamine (35.7 kg, 1 equivalent), followed by 412.9 kg THF. To the reaction mixture was charged a solution of 48.3 $K_2CO_3$ in 169 kg water. The acid chloride solution of described in the Alternative Preparation of 1-(4-Fluoro-phenylcarbamoyl)-cyclopropanecarbonyl chloride above was transferred to the reactor containing 4-(6,7-dimethoxy-quinoline-4-yloxy)-phenylamine while maintaining the temperature between 20-30° C. over a minimum of two hours. The reaction mixture was stirred at 20-25° C. for a minimum of three hours. The reaction temperature was then adjusted to 30-25° C. and the mixture was agitated. The agitation was stopped and the phases of the mixture were allowed to separate. The lower aqueous phase was removed and discarded. To the remaining upper organic phase was added 804 kg water. The reaction was left stirring at 15-25° C. for a minimum of 16 hours.

The product precipitated. The product was filtered and washed with a mixture of 179 kg water and 157.9 kg THF in two portions. The crude product was dried under a vacuum for at least two hours. The dried product was then taken up in 285.1 kg THF. The resulting suspension was transferred to reaction vessel and agitated until the suspension became a clear (dissolved) solution, which required heating to 30-35° C. for approximately 30 minutes. 456 kg water was then added to the solution, as well as 20 kg SDAG-1 ethanol (ethanol denatured with methanol over two hours. The mixture was agitated at 15-25° C. for at least 16 hours. The product was filtered and washed with a mixture of 143 kg water and 126.7 THF in two portions. The product was dried at a maximum temperature set point of 40° C.

In an alternative procedure, the reaction temperature during acid chloride formation was adjusted to 10-15° C. The recrystallization temperature was changed from 15-25° C. to 45-50° C. for 1 hour and then cooled to 15-25° C. over 2 hours.

Preparation of cyclopropane-1,1-dicarboxylic acid [4-(6,7-dimethoxy-quinoline-4-yloxy)-phenyl]-amide (4-fluoro-phenyl)-amide, malate salt Cyclopropane-1,1-dicarboxylic acid [4-(6,7-dimethoxy-quinoline-4-yloxy)-phenyl]-amide (4-fluoro-phenyl)-amide (1-5; 13.3 kg), L-malic acid (4.96 kg), methyl ethyl ketone (MEK; 188.6 kg) and water (37.3 kg) were charged to a reactor and the mixture was heated to reflux (approximately 74° C.) for approximately 2 hours. The reactor temperature was reduced to 50 to 55° C. and the reactor contents were filtered. These sequential steps described above were repeated two more times starting with similar amounts of starting material (13.3 kg), L-Malic acid (4.96 kg), MEK (198.6 kg) and water (37.2 kg). The combined filtrate was azeotropically dried at atmospheric pressure using MEK (1133.2 kg) (approximate residual volume 711 L; KF≤0.5 w/w) at approximately 74° C. The temperature of the reactor contents was reduced to 20 to 25° C. and held for approximately 4 hours resulting in solid precipitate which was filtered, washed with MEK (448 kg) and dried under vacuum at 50° C. to afford the title compound (45.5 kg).

Alternative Preparation of cyclopropane-1,1-dicarboxylic acid [4-(6,7-dimethoxy-quinoline-4-yloxy)-phenyl]-amide (4-fluoro-phenyl)-amide, (L) malate salt Cyclopropane-1,1-dicarboxylic acid [4-(6,7-dimethoxy-quinoline-4-yloxy)-phenyl]-amide (4-fluoro-phenyl)-amide (47.9 kg), L-malic acid (17.2), 658.2 kg methyl ethyl ketone, and 129.1 kg water (37.3 kg) were charged to a reactor and the mixture was heated 50-55° C. for approximately 1-3 hours, and then at 55-60° C. for an additional 4-5 hours. The mixture was clarified by filtration through a 1 µm cartridge. The reactor temperature was adjusted to 20-25° C. and vacuum distilled with a vacuum at 150-200 mm Hg with a maximum jacket temperature of 55° C. to the volume range of 558-731 L.

The vacuum distillation was performed two more times with the charge of 380 kg and 380.2 kg methyl ethyl ketone, respectively. After the third distillation, the volume of the batch was adjusted to 18 v/w of cyclopropane-1,1-dicarboxylic acid [4-(6,7-dimethoxy-quinoline-4-yloxy)-phenyl]-amide (4-fluoro-phenyl)-amide by charging 159.9 kg methyl ethyl ketone to give a total volume of 880 L. An additional vacuum distillation was carried out by adjusting 245.7 methyl ethyl ketone. The reaction mixture was left with moderate agitation at 20-25° C. for at least 24 hours. The product was filtered and washed with 415.1 kg methyl ethyl ketone in three portions. The product was dried under a vacuum with the jacket temperature set point at 45° C.

In an alternative procedure, the order of addition was changed so that a solution of 17.7 kg L-malic acid dissolved in 129.9 kg water was added to cyclopropane-1,1-dicarboxylic acid [4-(6,7-dimethoxy-quinoline-4-yloxy)-phenyl]-amide (4-fluoro-phenyl)-amide (48.7 kg) in methyl ethyl ketone (673.3 kg).

Example 1

Testing of an Compound 1 in Both Osteoclast and Osteoblast Differentiation and Activity Assays In Vitro The objective of this study was to investigate the effects of 7 concentrations of Compound 1 on differentiation and activity of human osteoclasts and mouse osteoblasts in vitro. The following concentrations were tested: 0.004, 0.012, 0.037, 0.11, 0.33, 1.0 and 3.0 µM. The study was performed using human bone marrow-derived CD34+ osteoclast precursor cells that were cultured on bovine bone slices, and KS483 mouse osteoprogenitor cells that were induced to differentiate into bone-forming osteoblasts.

The study was performed in four parts. In the first part, human bone marrow-derived CD34+ osteoclast precursor cells were cultured on bovine bone slices for 7 days, after which the formed osteoclasts were quantitated by measuring tartrate-resistant acid phosphatase 5b activity (TRACP 5b) in the culture medium. This assay demonstrates the effects of Compound 1 on osteoclast differentiation. Osteoprotegerin (OPG) was included as a reference inhibitor of osteoclast differentiation to demonstrate that the culture system works as expected.

In the second part, the culture medium of human osteoclasts was replaced by new medium at day 7, and the formed mature osteoclasts were cultured for an additional 3 days, allowing them to resorb bone. Compound 1 was added into the culture medium at day 7. This assay demonstrates the effects of Compound 1 on bone-resorbing activity of mature osteoclasts. C-terminal cross-linked telopeptides of type I collagen (CTX) were measured in the culture medium collected at day 10 to quantitate bone resorption during days 7-10. TRACP 5b was measured at day 7 to quantitate osteoclast number before Compound 1 was added. The CTX values were divided by the TRACP 5b values, resulting as a resorption index that indicates mean osteoclast activity. The cysteine protease inhibitor E64 was included as a reference inhibitor of osteoclast activity to demonstrate that the culture system works as expected.

In the third part, KS483 mouse osteoprogenitor cells were cultured for 8 days, after which the formed mature osteoblasts were quantitated by measuring the amount of intracellular alkaline phosphatase (ALP) activity. This assay demonstrates the effects of Compound 1 on osteoblast differentiation. 17ß-estradiol was included in the study as a reference compound that stimulates osteoblast differentiation to demonstrate that the culture system works as expected.

In the fourth part of the study, KS483 mouse osteoprogenitor cells were cultured for 13 days, during which N-terminal propeptide of type I procollagen (PINP) secreted into the culture medium was determined at day 11 to demonstrate effects on organic bone matrix formation, and the amount of calcium deposited into the formed bone matrix was determined at day 13 to demonstrate effects on inorganic bone matrix formation. This osteoblast activity assay demonstrates the effects of Compound 1 on bone formation activity of osteoblasts. 17β-estradiol was included in the study as a reference compound that stimulates osteoblast differentiation and activity, to demonstrate that the culture system works as expected.

Compound 1 showed a dose-dependent inhibition of osteoclast differentiation that was significant with 0.11, 0.33, 1.0 and 3.0 µM concentrations. Microscopic analysis showed that the 0.11 and 0.33 µM concentrations did not affect the number of Hoechst and TRACP positive mononuclear cells, suggesting specific inhibition of osteoclast differentiation. However, the 1.0 and 3.0 µM concentrations decreased the number of both Hoechst and TRACP positive mononuclear cells, suggesting that the inhibitory effects observed with these concentrations are at least partly cytotoxic. No effects were observed in the osteoclast activity assay.

Compound 1 showed a dose-dependent stimulation of osteoblast differentiation and activity. Compound 1 concentrations 0.012, 0.037, 0.11, 0.33 and 1.0 µM increased and the concentration 3.0 µM decreased ALP values in the osteoblast differentiation assay. In osteoblast activity assay, concentrations 0.012 and 0.037 µM increased PINP values, and concentrations 0.004, 0.012, 0.037 and 0.11 µM increased calcium values. The concentrations 0.33, 1.0 and 3.0 µM decreased both PINP and calcium values. These results demonstrate that 0.004, 0.012, 0.037 and 0.11 µM concentrations of Compound 1 have beneficial effects on bone cells, activating osteoblastic bone formation and having no effects or inhibiting formation of bone-resorbing osteoclasts.

Description of Study

The objective of this study was to investigate the effects of Compound 1 selected by the Sponsor on differentiation and activity of human osteoclasts and mouse osteoblasts in vitro. The effects on osteoclasts were studied using a model where bone marrow-derived human osteoclast precursor cells are cultured on bovine bone slices for 7 days in conditions favouring osteoclast differentiation, and allowed to differentiate into bone-resorbing osteoclasts. After completion of osteoclast differentiation at day 7, the culture medium was removed and new culture medium favouring osteoclast activity was added into the wells. The mature osteoclasts were then cultured for an additional 3 days, allowing them to resorb bone. In the osteoclast differentiation assay, the test compounds and a reference inhibitor osteoprotegerin (OPG) were added into cultures at day 0. In the osteoclast activity assay, the test compounds and a reference inhibitor E64 were added into cultures at day 7. Seven concentrations in 8 replicates were tested in both assays. Tartrate-resistant acid phosphatase 5b activity (TRACP 5b) was measured from the culture medium collected at day 7 as an index of the number of osteoclasts formed in each well during the differentiation period. C-terminal cross-linked telopeptides of type I collagen (CTX) was measured from the culture medium collected at day 10 to quantitate bone resorption during days 7-10.

The effects on osteoblasts were studied using KS483 mouse osteoprogenitor cells that can be induced to differentiate into bone-forming osteoblasts. 17ß-estradiol (E2) was included in the study as a reference compound that stimulates osteoblast differentiation and activity, to demonstrate that the culture systems can detect stimulation of osteoblast differentiation and activity. In the osteoblast differentiation assay, the cells were cultured for 8 days, after which the formed mature osteoblasts were quantitated by measuring the amount of intracellular alkaline phosphatase (ALP) activity. In the osteoblast activity assay, osteoprogenitor cells were cultured for 13 days, during which N-terminal propeptide of type I procollagen (PINP) secreted into the culture medium was determined at day 11 to demonstrate effects on organic bone matrix formation, and the amount of calcium deposited into the formed bone matrix was determined at day 13 to demonstrate effects on inorganic bone matrix formation.

The tests were performed in 96-well plates containing a baseline group including vehicle, a control group including the reference compound, and the groups including test compound. The reference compounds were included to demonstrate that the test systems work as expected. In osteoclast cultures, the study was approved if the results of the control group were significantly lower than the results of the baseline group. In osteoblast cultures, the study was approved if the results of the control group were significantly higher than the results of the baseline group.

Compound 1

Compound 1 was obtained from the Sponsor as a solid compound. The compound was suspended to DMSO at a concentration of 10 mM to obtain a stock solution. Fresh stock solution was made prior to tests, that was stored dry in dark at room temperature. For long-term (greater than 5 days), the stock solution was stored in −70° C. Appropriate dilutions were prepared from the stock solution to obtain the desired test concentrations; 0.004 µM, 0.012 µM, 0.037 µM, 0.11 µM, 0.33 µM, 1 µM and 3 µM.

Reference Compounds

Osteoprotegerin (OPG, 5 nM, catalogue number 450-14, obtained from PeproTech EC Ltd, London, UK) was used as a reference inhibitor of osteoclast differentiation and the cysteine protease inhibitor E64 (1_M, catalogue number E-3132, obtained from Sigma-Aldrich, St Louis, Mo., USA) as a reference inhibitor of the resorption activity of osteoclasts.

17ß-estradiol (E2; 10 nM, catalogue number E1024, obtained from Sigma-Aldrich, St Louis, Mo., USA) was used as a reference stimulator of osteoblast differentiation and activity.

Method

Osteoclast Cultures

The method of osteoclast culture on bone slices was originally described by Boyde and co-workers (1984) and by Chambers and co-workers (1984). Originally, the number of osteoclasts was determined by calculating the number of tartrate-resistant acid phosphatase (TRACP)-positive multi-nuclear cells under a microscope. Later, it was demonstrated that secreted TRACP 5b activity reflects the number of osteoclasts in mouse osteoclast cultures (Alatalo et al. 2000). While secreted TRACP 5b activity correlated strongly with the number of osteoclasts, TRACP 5b was not secreted by TRACP-positive mononuclear osteoclast precursor cells before they had differentiated into mature multinuclear osteoclasts. Therefore, secreted TRACP 5b is a reliable marker of the number of mature multinuclear osteoclasts.

The rate of bone resorption in the cultures was originally determined by counting the number of resorption pits on each bone or dentine slice using a microscope with phase contrast objectives. Later, the pits were visualized using Wheat Germ Agglutinin lectin that specifically binds to the resorbed area inbone, making it possible to quantitate the total resorbed area using a microscope and computer-assisted image analysis system. These methods have two disadvantages: They are time-consuming and they cannot detect differences in the depth of the resorption pits, which may cause false results. Later, it was demonstrated that C-terminal cross-linked telopeptides of type I collagen (CTX) quantitate bone collagen degradation products released into the culture medium (Bagger et al. 1999). This method is rapid and sensitive, and it is a reliable parameter of total resorbed volume (including depth of pits).

A human osteoclast culture system was developed for use in this study where CD34+ osteoclast precursor cells derived from human bone marrow (Poietics® Human Osteoclast Precursors, Lonza, Walkersville, USA) are cultured on bovine bone slices in the presence of appropriate growth factors, including M-CSF and RANK-ligand (Rissanen et al. 2009). The cells are first allowed to differentiate into mature bone-resorbing osteoclasts, and the formed osteoclasts are then allowed to resorb bone. The test and reference compounds are added into the cell cultures at the beginning of the differentiation and/or the resorption period, and their effects on the differentiation and/or resorbing activity of osteoclasts are determined.

Secreted TRACP 5b is determined from the culture medium after the differentiation period using a commercially available method (BoneTRAPÒ, IDS Ltd, Boldon, UK). Secreted TRACP 5b describes accurately the number of osteoclasts formed in each well during the differentiation period. CTX is determined from the culture medium after the resorption period using a commercially available method (CrossLapsÒ for cultures, IDS Ltd, Boldon, UK). CTX describes accurately the amount of bone collagen degradation products released into the culture medium in each well during the resorption period. A resorption index demonstrating mean osteoclast activity (Rissanen et al. 2009) is calculated by dividing the obtained resorption volume (CrossLapsÒ value) with the number of osteoclasts (BoneTRAPÒ value).

Osteoblast Cultures

Osteoblasts are bone forming cells which arise from mesenchymal stem cells. During the development of osteoblasts, three distinct periods have been defined: 1) cell proliferation and secretion of extracellular matrix (ECM); 2) ECM maturation; 3) ECM mineralization. During these periods, a sequential expression of osteoblast phenotype markers has been characterized. Alkaline phosphatase (ALP) is associated with the bone cell phenotype and is actively expressed during the maturation of the osteoblast. N-terminal propeptide of type I procollagen (P1NP) is a marker of type I collagen synthesis and ECM production and a relevant measure for assessment of new osteoporosis drug candidates in preclinical studies (Rissanen et al. 2008). With the onset of mineralization, large amounts of calcium and hydroxyapatite are deposited into the mature organic matrix to form bone-like nodules. Following these markers, it is possible to study all stages of osteoblast differentiation and activity in a culture system.

Several model systems were set up to study osteoblasts. Isolation of cells with the osteoblastic phenotype from calvaria was the very first attempt. However, these cells only represent the mature stage of osteoblasts, because only a small fraction of the calvarial cells are osteoblast precursors (Bellows et al. 1989). Alternatively, mesenchymal bone marrow cells or progenitor cell lines can be stimulated to differentiate into osteoblastic cells. KS483 cells, cloned from mouse calvaria, are estrogen responsive osteoblast precursors that are able to differentiate into bone-forming osteoblasts and form mineralized bone nodules in vitro (Dang et al. 2002).

A culture system was established that can be used as an in vitro model for studying the effects of anabolic and estrogen-like compounds on osteoblast differentiation and activity. In this culture system mouse KS483 cells first proliferate and then differentiate into osteoblasts capable of forming mineralized bone nodules in the presence of ascorbic acid and ß-glycerophosphate (Fagerlund et al. 2009). The test and reference compounds are added into the cell cultures concomitantly with the medium change, and their effects on the differentiation and activity of osteoblasts are determined. Cellular ALP, a marker of osteoblast differentiation, is determined from the cell lysates as described earlier (Lowry et al. 1954). Secreted PINP, a marker of organic bone matrix formation, is determined from the culture medium using a commercially available method (Rat/Mouse PINP EIA, IDS Ltd, Boldon, UK). Calcium deposition, an index of inorganic bone matrix formation, is measured using a commercially available calcium assay (Roche Diagnostics).

Procedures

Osteoclast Differentiation Assay

In this study, human bone marrow-derived CD34+ stem cells (10000 cells/well) were suspended in culture medium and allowed to attach to bovine bone slices in 96-well tissue culture plates. The culture medium (containing 10% FBS, OCP BulletKit® Lonza, Walkersville, USA) was supplemented with appropriate amounts of important growth factors favoring osteoclast differentiation and activity, including M-CSF (33 ng/ml, OCP BulletKit® Lonza, Walkersville, USA) and RANK-ligand (66 ng/ml, OCP BulletKit® Lonza, Walkersville, USA) in 200 µl of medium. The cells were incubated in a CO2 incubator in humidified atmosphere of 95% air and 5% carbon dioxide at 37° C. for 7 days. The test compounds and reference compound OPG were added at day 0. Supernatants collected at day 7 were stored at −70° C. until analysis of TRACP 5b. TRACP 5b was measured from the culture medium (20 µl/sample) using VICTOR2™ Multilabel Counter (PerkinElmer, Waltham, Mass., USA). Cells were fixed with 3% paraformaldehyde and stained for TRACP activity (Leucocyte acid phosphatase kit; Sigma Aldrich, St Louis, Mo., USA) and Hoechst 33258 (Sigma Aldrich, St Louis, Mo., USA).

The following groups were included (each group contains 8 replicates):
Plate 1:
1) Baseline group with vehicle (DMSO)
2) Control group with 5 nM OPG
3) 0.004 µM Compound 1
4) 0.012 µM Compound 1
5) 0.037 µM Compound 1
6) 0.11 µM Compound 1
7) 0.33 µM Compound 1
8) 1.0 µM Compound 1
9) 3.0 µM Compound 1

Osteoclast Activity Assay

In this study, human bone marrow-derived CD34+ stem cells (10000 cells/well) were suspended in culture medium and allowed to attach to bovine bone slices in 96-well tissue culture plates. The culture medium (containing 10% FBS, OCP BulletKit® Lonza, Walkersville, USA) was supplemented with appropriate amounts of important growth factors favoring osteoclast differentiation and activity, including M-CSF (33 ng/ml, OCP BulletKit® Lonza, Walkersville, USA) and RANK-ligand (66 ng/ml, OCP BulletKit® Lonza, Walkersville, USA) in 200 µl of medium. The cells were incubated in a CO2 incubator in humidified atmosphere of 95% air and 5% carbon dioxide at 37° C. After completion of osteoclast differentiation at day 7, all culture medium was removed and new 200 µl of culture medium favouring osteoclast activity was added into the wells.

The mature osteoclasts were cultured for an additional 3 days, allowing them to resorb bone. The test compounds and reference compound E64 were added at day 7, after completion of the osteoclast differentiation period. Supernatants collected at day 7 and day 10 were stored at −70° C. until analysis of TRACP 5b and CTX. TRACP 5b was measured from the culture medium (20 µl/sample) collected at day 7 and CTX from the culture medium (50 µl/sample) collected at day 10 using VICTOR2™ Multilabel Counter (PerkinElmer, Waltham, Mass., USA).

The following groups were included (each group contains 8 replicates):
Plate 1:
1) Baseline group with vehicle (DMSO)
2) Control group with 1_M E64
3) 0.004 µM Compound 1
4) 0.012 µM Compound 1
5) 0.037 µM Compound 1
6) 0.11 µM Compound 1
7) 0.33 µM Compound 1
8) 1.0 µM Compound 1
9) 3.0 µM Compound 1

Osteoblast Differentiation Assay

Mouse KS483 cells were cultured in T-75 tissue culture flasks in aMEM supplemented with 10% charcoal-stripped fetal bovine serum until 80-90% confluence. The cells were incubated in a CO2 incubator in humidified atmosphere of 95% air and 5% carbon dioxide at 37° C. After reaching 80-90% confluence, subcultures were prepared. Cells were removed from the flasks with trypsin treatment and counted. For induction of the maturation of osteoblasts and bone formation, the immature osteoblastic cells were plated in type I collagen-coated 96-well plates. The cells were cultured for 8 days with a supplement of ascorbic acid (50 g/ml), and half of the media was changed every 3-4 days. The test compound and control substance (E2) were added in the beginning of the culture period and when the medium was changed. The cultures were stopped at day 8 by removing the culture media from the wells, and cell lysates were prepared. Cellular ALP activity and total protein content (Protein Assay, Bio-Rad Laboratories Inc, CA, USA) were quantitated by using VICTOR2™ Multilabel Counter (PerkinElmer, Waltham, Mass., USA).

The following groups were included (each group contains 8 replicates):
Plate 1:
1) Baseline group with vehicle (DMSO)
2) Control group with 10 nM E2
3) 0.004 µM Compound 1
4) 0.012 µM Compound 1
5) 0.037 µM Compound 1
6) 0.11 µM Compound 1
7) 0.33 µM Compound 1
8) 1.0 µM Compound 1
9) 3.0 µM Compound 1

Osteoblast Activity Assay

Mouse KS483 cells were cultured in T-75 tissue culture flasks in aMEM supplemented with 10% charcoal-stripped fetal bovine serum until 80-90% confluence. The cells were incubated in a CO2 incubator in humidified atmosphere of 95% air and 5% carbon dioxide at 37° C. After reaching 80-90% confluence, subcultures were prepared. Cells were removed from the flasks with trypsin treatment and counted. For induction of the maturation of osteoblasts and bone formation, the immature osteoblastic cells were plated in type I collagen-coated 96-well plates. The cells were cultured for 13 days with a supplement of ascorbic acid (50 µg/ml) and ß-glycerophosphate (5 mM), and half of the media was changed every 3-4 days. The test compound and control substance (E2) were added in the beginning of the culture period and when the medium was changed. Secreted PINP was measured from the culture medium at day 11 as a marker of organic bone matrix formation. The cultures were stopped at day 13 by removing the culture media from the wells and adding hydrochloric acid. Calcium deposited into the formed bone matrix was quantitated by using VICTOR2™ Multilabel Counter (PerkinElmer, Waltham, Mass., USA).

The following groups were included (each group contains 8 replicates):

Plate 1:
1) Baseline group with vehicle (DMSO)
2) Control group with 10 nM E2
3) 0.004 µM Compound 1
4) 0.012 µM Compound 1
5) 0.037 µM Compound 1
6) 0.11 µM Compound 1
7) 0.33 µM Compound 1
8) 1.0 µM Compound 1
9) 3.0 µM Compound 1

Statistical Analysis

All relevant data is presented as figures and/or tables [mean, standard deviation (SD) and statistical significance] with units. Statistical analyses were performed with Origin statistical software (OriginLab Corporation, Northampton, Mass., USA). One-way analysis of variance (ANOVA) was used to study if the values obtained between different groups (baseline vs. reference inhibitor and test compounds) were statistically different (with p<0.05). If the one-way ANOVA revealed statistically significant differences, t-test was used for statistical comparisons between groups.

Results

The effect of Compound 1 on osteoclast differentiation was measured at day 7 as depicted in FIG. 1. The results are shown as TRACP 5b activity (U/L) secreted in the culture medium. In this and other figures, BL means baseline (no added compounds); C means Control (5.0 nM OPG). The results were compared to the BL using one-way ANOVA (p less than 0.001 between all groups). Three asterisks (*) indicate a statistically significant inhibitory effect with a p-value of less than 0.001. Two asterisks () indicate a statistically significant effect with a p-value of less than 0.01. One asterisk (*) indicates a p-value of less than 0.05. Asterisks with parentheses in the Figure ([***]) indicate a significant difference opposite to baseline level.

The results are further summarized in Table 1. As in the Figure, three asterisks ([*]) indicate a statistically significant inhibitory effect with a p-value of less than 0.001. As in the figures, and in this and other tables, three asterisks (*) indicate a statistically significant inhibitory effect with a p-value of less than 0.001; two asterisks (**) indicate a statistically significant effect with a p-value of less than 0.01; one asterisk (*) indicates a p-value of less than 0.05. Asterisks with parentheses in the Figure ([***]) indicate a significant difference opposite to baseline level.

TABLE 1

Osteoclast Differentiation Assay. TRACP 5b Activity at Day 7.

| | Compound 1 Concentration (µM) | | | | | | |
|---|---|---|---|---|---|---|---|
| | 0.004 | 0.012 | 0.037 | 0.11 | 0.33 | 1.0 | 3.0 |
| Percent Activity (%) Compared to BL | 85 | 80 | 74 | 45(*) | 15(*) | 4(*) | 0(*) |

Figure 2:
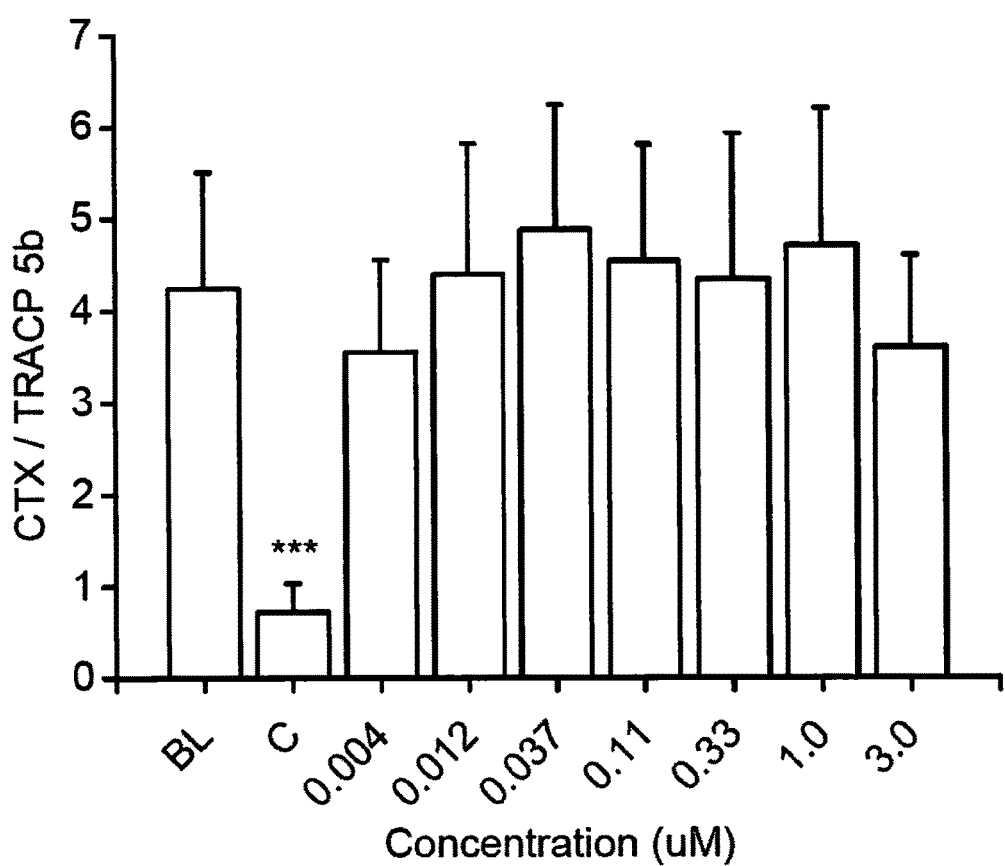
FIG. 2 depicts the effect of Compound 1 on the resorbing activity of human osteoclasts at day 7 as CTX/TRACP 5b values.

The effect of Compound 1 on the resorbing activity of human osteoclasts is depicted in FIG. 2. The results are shown as CTX/TRACP 5b values. The CTX values were determined at the end of the resorption period at day 10, and the TRACP values at the beginning of the resorption period at day 7. The results are further summarized in Table 2.

TABLE 2

Osteoclast Differentiation Assay. CTX at Day 10 and TRACP 5b Activity at Day 7.

| | Compound 1 Concentration (µM) | | | | | | |
|---|---|---|---|---|---|---|---|
| | 0.004 | 0.012 | 0.037 | 0.11 | 0.33 | 1.0 | 3.0 |
| Percent Activity (%) Compared to BL | 84 | 104 | 115 | 107 | 102(*) | 111(*) | 85(***) |

Figure 3:
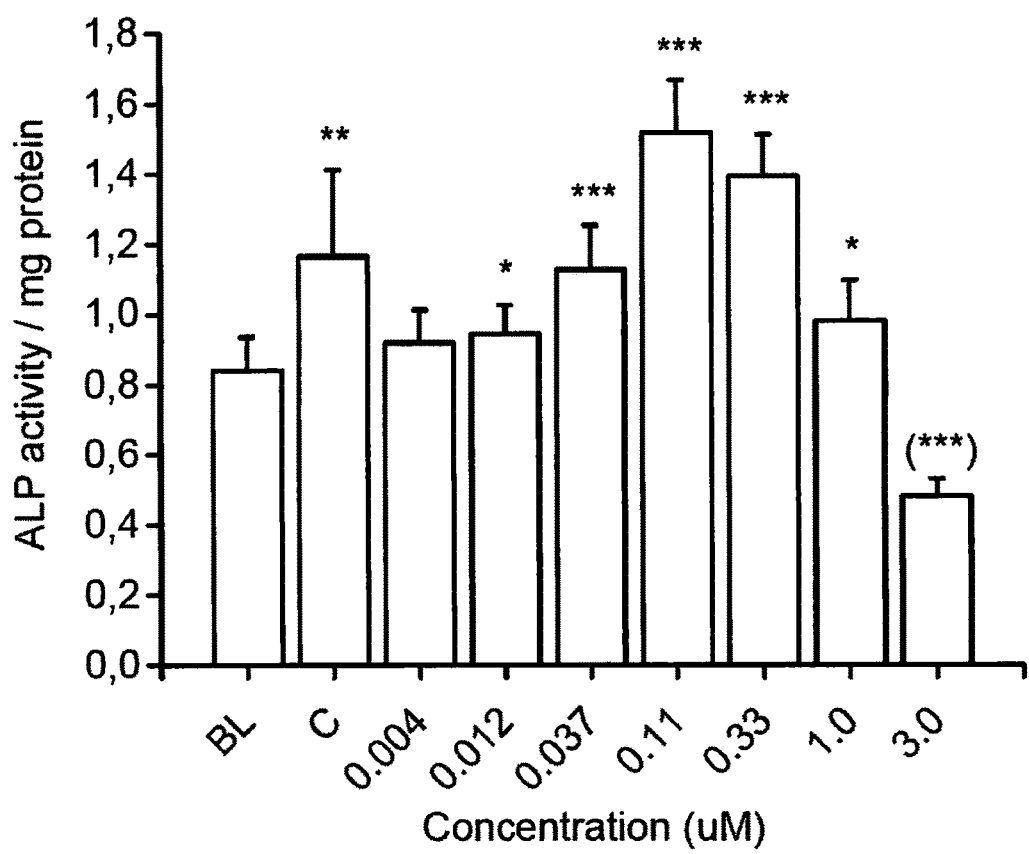
FIG. 3 depicts the effect of Compound 1 on osteoblast differentiation at day 8 as cellular ALP activity/mg protein.

The effect of Compound 1 on osteoblast differentiation at day 8 is depicted in FIG. 3. The results are shown as cellular ALP activity/mg protein. The results are further summarized in Table 3.

TABLE 3

Osteoblast Differentiation Assay. ALP Activity at Day 8.

| | Compound 1 Concentration (µM) | | | | | | |
|---|---|---|---|---|---|---|---|
| | 0.004 | 0.012 | 0.037 | 0.11 | 0.33 | 1.0 | 3.0 |
| Percent Activity (%) Compared to BL | 109 | 113 | 134(*) | 181(*) | 166(***) | 117(*) | 57([***]) |

Figure 4:
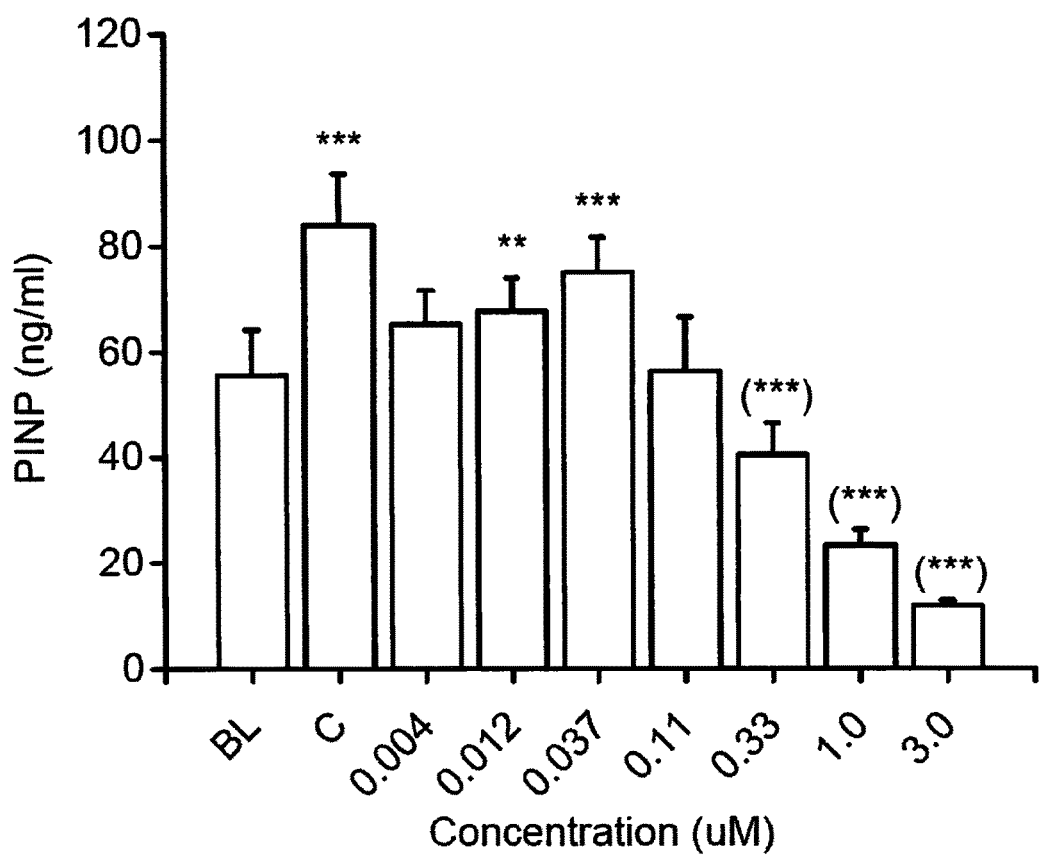
FIG. 4 depicts the effect of Compound 1 on bone forming activity of mouse osteoblasts at day 11 as PINP secreted into the culture medium.

The effect of Compound 1 on bone forming activity of mouse osteoblasts is depicted in FIG. 4. The results are shown as PINP secreted into the culture medium at day 11. The results are further summarized in Table 4.

TABLE 4

Osteoblast Differentiation Assay. PINP Activity at Day 11.

| | Compound 1 Concentration (µM) | | | | | | |
|---|---|---|---|---|---|---|---|
| | 0.004 | 0.012 | 0.037 | 0.11 | 0.33 | 1.0 | 3.0 |
| Percent Activity (%) Compared to BL | 117 | 122() | 135(*) | 101 | 73([]) | 42([*]) | 21([***]) |

Figure 5:
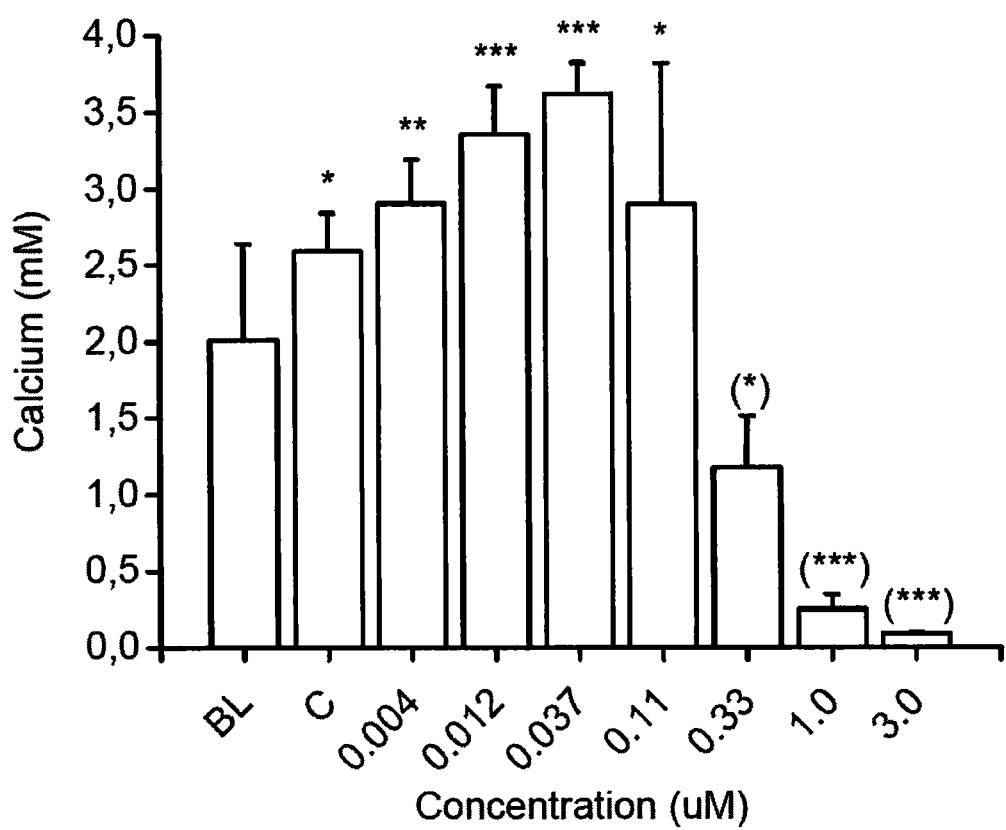
FIG. 5 depicts the effect of Compound 1 on bone forming activity of mouse osteoblasts at day 13 as calcium deposition at day 13.

The effect of Compound 1 on bone forming activity of mouse osteoblasts is depicted in FIG. 5. The results are shown as calcium deposition at day 13. The results are shown as PINP secreted into the culture medium at day 11. The results are further summarized in Table 4.

TABLE 5

Osteoblast Differentiation Assay. Calcium Deposition at Day 13.

| | Compound 1 Concentration (µM) | | | | | | |
|---|---|---|---|---|---|---|---|
| | 0.004 | 0.012 | 0.037 | 0.11 | 0.33 | 1.0 | 3.0 |
| Percent Activity (%) Compared to BL | 145(*) | 167(*) | 180(***) | 144(*) | 59([]) | 12([*]) | 4([***]) |

CONCLUSION

The reference inhibitors OPG and E64 inhibited significantly osteoclast differentiation and activity, respectively, and the reference stimulator 17β-estradiol stimulated significantly osteoblast differentiation and activity describing that the assays were performed successfully and the results obtained are reliable. Compound 1 showed a dose-dependent inhibition of osteoclast differentiation that was significant with 0.11, 0.33, 1.0 and 3.0 µM concentrations. Microscopic analysis showed that the 0.11 and 0.33 µM concentrations of Compound 1 did not affect the number of Hoechst and TRACP positive mononuclear cells, suggesting specific inhibition of osteoclast differentiation. However, the 1.0 and 3.0 µM concentrations decreased the number of both Hoechst and TRACP positive mononuclear cells, suggesting that the inhibitory effects observed with these concentrations are at least partly cytotoxic.

Compound 1 had no effects on osteoclast resorption activity with the tested concentrations. Compound 1 showed a dose-dependent stimulation of osteoblast differentiation with 0.012, 0.037, 0.11, 0.33 and 1.0 µM concentrations and inhibitory effects with 3.0 µM concentration. Compound 1 showed a dose-dependent stimulation of bone forming activity of osteoblasts with 0.004, 0.012 0.037 and 0.11 µM concentrations, and inhibitory effects with 0.33, 1.0 and 3.0 µM concentrations. As a conclusion, the 0.004, 0.012, 0.037 and 0.11 µM concentrations of Compound 1 showed beneficial effects on bone cells, activating osteoblastic bone formation and having no effects or inhibiting formation of bone-resorbing osteoclasts.

REFERENCES

Alatalo S L, Halleen J M, Hentunen T A, Mönkkönen J, Väänänen HK (2000) Rapid screening method for osteoclast differentiation in vitro that measures tartrate-resistant acid phosphatase 5b activity secreted into the culture medium. Clin Chem 46:1751-1754.

Bagger Y Z, Foged N T, Andersen L, Lou H, Qvist P (1999) CrossLaps for culture: An improved enzyme-linked immunosorbent assay (ELISA) for measuring bone resorption in vitro. J Bone Miner Res 14, Suppl. 1, S370.

Bellows C G, Aubin J E (1989) Determination of the number of osteoprogenitors in isolated fetal rat calvarial cells in vitro. Develop Biol 113:8-13.

Boyde A, Ali N N, Jones S J (1984) Resorption of dentine by isolated osteoclasts in vitro. Br Dent J 156:216-220.

Chambers T J, Revell P A, Fuller K, Athanasou N A (1984) Resorption of bone by isolated rabbit osteoclasts. J Cell Sci 66:383-399.

Dang Z C, Van Bezooijen R L, Karperien M, Papapoulos S E, Löwik C W G M (2002) Exposure of KS483 cells to estrogen enhances osteogenesis and inhibits adipogenesis. J Bone Miner Res 17:394-405.

Fagerlund K M, Rissanen J P, Suutari T, Chan A, Halleen J M (2009) Validation of an in vitro osteoblast culture model using estrogen responsive KS483 mouse osteoblast precursor cell line. J Bone Miner Res 24 (Suppl 1). Available at http://www.asbmr.org/Meetings/AnnualMeeting/AbstractDetail.aspx?a id=9815c5a5-00eb4952-b1aa-838899f5e151. Accessed Oct. 1, 2009.

Lowry O H, Roberts N R, Wu M L, Hixon W S, Crawford E J (1954) The quantitative histochemistry of brain. II. Enzyme measurements. J Biol Chem 207:19-37.

Rissanen J P, Suominen M I, Peng Z, Morko J, Rasi S, Risteli J, Halleen J M (2008) Short-term changes in serum PINP predict long-term changes in trabecular bone in the rat ovariectomy model. Calcif Tissue Int 82:155-161.

Rissanen J P, Ylipahkala H, Fagerlund K M, Long C, Väänänen H K, Halleen J M (2009) Improved methods for testing antiresorptive compounds in human osteoclast cultures. J Bone Miner Metab 27:105-109.

Example 2

Short-Term Effects of Compound 1 on Bone Turnover Markers in the Rat Ovariectomy (OVX) Model The objective of this study was to investigate short-term effects of Compound 1 on biochemical serum markers of bone metabolism in a prevention study in a rat ovariectomy (OVX) model for postmenopausal osteoporosis. 17β-estradiol (E2) was used as a reference compound. The following five experimental groups were included in the study:

1) SHAM-operated control rats receiving vehicle (5 ml/kg/d p.o.)
2) OVX control rats receiving vehicle (5 ml/kg/d p.o.)
3) OVX control rats receiving 17β-estradiol (4 μg/kg/d s.c.)
4) OVX rats receiving test compound Compound 1 (1 mg/kg/d p.o.)
5) OVX rats receiving test compound Compound 1 (3 mg/kg/d p.o.)

Each group contained eight female rats (Sprague-Dawley) that were three months of age at the beginning of in-life phase of the study. Before the start of the in-life phase, animals were weighed, their blood samples were harvested, and animals were randomized to study groups by stratification according to body weight and serum levels of procollagen type I N-terminal propeptide (PINP). At the beginning of the in-life phase, animals were weighed and operated. Treatment was started one day after the operations and continued once a day for two weeks. Sterile water was used as vehicle in groups 1 and 2. Body weight was determined after one week of treatment and treatment doses were adjusted accordingly. After two weeks of treatment, animals were weighed, their blood samples were harvested, animals were terminated, and their relative uterine weight was determined. For analyzing short-term effects of treatments, levels of four bone metabolism biomarkers were determined in serum samples harvested before the start and at the end of the in-life phase. These biomarkers included PINP as a marker of bone formation, N-terminal mid-fragment of osteocalcin (OC) as a general marker of bone turnover, C terminal cross-linked telopeptides of type I collagen (CTX) as a marker of bone resorption, and tartrate-resistant acid phosphatase isoform 5b (TRACP 5b) as a marker of osteoclast number. Serum levels at day −7 were used as baseline levels and serum levels at day 14 as levels affected by operations and treatments.

Surgical ovariectomy increased body weight, decreased relative uterine weight, increased serum levels of CTX, OC and PINP, and decreased serum TRACP 5b activity in female rats after two post-surgery weeks. These bone metabolism biomarker results indicate that the ovariectomy enhanced bone resorption, increased bone turnover and bone formation, and decreased the total number of osteoclasts. These conclusions imply that the surgical ovariectomy accelerated the rate of bone turnover in female rats.

The short-term effects of 17β-estradiol were studied by comparing OVX animals treated with 17β-estradiol at the subcutaneous dose of 4 μg/kg/d with OVX animals treated with vehicle. The 17β-estradiol treatment had the following effects on body weight, relative uterine weight and bone metabolism biomarkers in OVX rats:

Treatment with 17β-estradiol prevented the OVX-induced gain in body weight and the OVX-induced reduction in relative uterine weight.
Treatment with 17β-estradiol prevented the OVX-induced increase in serum CTX, OC and PINP levels.
Treatment with 17β-estradiol did not affect the OVX-induced reduction in serum TRACP 5b activity.

The bone metabolism biomarker results indicate that treatment with 17β-estradiol at the subcutaneous dose of 4 μg/kg/d prevented the OVX-induced enhancement in bone resorption and the OVX-induced increase in bone turnover and bone formation, but did not affect the OVX-induced reduction in the total number of osteoclasts in OVX rats after two weeks of treatment. These conclusions imply that treatment with 17β-estradiol at the subcutaneous dose of 4 μg/kg/d prevented the OVX-induced acceleration in the rate of bone turnover in female rats.

The short-term effects of Compound 1 were studied by comparing OVX animals treated with Compound 1 at the oral doses of 1 and 3 mg/kg/d with OVX animals treated with vehicle. The Compound 1 treatment had the following effects on body weight, relative uterine weight and bone metabolism biomarkers in OVX rats:

Treatment with Compound 1 at the oral dose of 1 mg/kg/d partially prevented the OVX-induced gain in body weight.
Treatment with Compound 1 at the oral doses of 1 and 3 mg/kg/d did not affect the OVX-induced reduction in relative uterine weight.
Treatment with Compound 1 at the oral dose of 3 mg/kg/d enhanced the OVX-induced increase in serum PINP levels and the OVX-induced reduction in serum TRACP 5b activity.
Treatment with Compound 1 at the oral doses of 1 and 3 mg/kg/d did not affect the OVX-induced increase in serum CTX and OC levels.

The bone metabolism biomarker results indicate that treatment with Compound 1 at the oral dose of 3 mg/kg/d enhanced the OVX-induced increase in bone formation and the OVX-induced reduction in the total number of osteoclasts, but did not affect the OVX-induced increase in bone resorption and bone turnover in OVX rats after two weeks of treatment. The enhanced bone formation in association with the reduced total number of osteoclasts and the unaltered levels of bone resorption imply that treatment with Compound 1 at the oral dose of 3 mg/kg/d shifted the OVX-stimulated bone turnover towards bone formation in female rats.

Description

Human osteoporosis is a systemic skeletal disease characterized by low bone mass and deterioration of bone microarchitecture, which leads to bone fragility and increased risk for fracture (Raisz et al. 2008). The chronic nature of osteoporosis makes it increasingly expensive for the society. As the expected lifetime is estimated to increase, the frequency of osteoporosis is also estimated to increase causing additional burden to our health care. Although effective therapies are already available for the treatment of osteoporosis, new therapies are needed with improved therapeutic window, i.e. improved efficacy/safety ratio. Preclinical efficacy studies with animal models for osteoporosis provide first-hand information about effects of new potential therapies before proceeding with them to clinical trials (Rissanen and Halleen 2010). Regulatory authorities of drug administration have approved gonadectomized rats suffering from osteopenia to be used as a predictive small animal model in testing the preclinical efficacy of new potential therapies for the treatment of osteoporosis.

The objective of this study was to investigate short-term effects of Compound 1 on biochemical serum markers of bone metabolism in a prevention study in a rat ovariectomy (OVX) model for postmenopausal osteoporosis. 17β-estradiol (E2) was used as a reference compound (Lindsay and Cosman 2008). The following five experimental groups were included in the study:

1) SHAM-operated control rats receiving vehicle (5 ml/kg/d p.o.)
2) OVX control rats receiving vehicle (5 ml/kg/d p.o.)

3) OVX control rats receiving 17β-estradiol (4 µg/kg/d s.c.)
4) OVX rats receiving Compound 1 (1 mg/kg/d p.o.)
5) OVX rats receiving Compound 1 (3 mg/kg/d p.o.)

Each group contained eight female rats (Sprague-Dawley) that were three months of age at the beginning of in-life phase of the study. The experimental design of the study is presented in FIG. 1. Animals were randomized to study groups by stratification according to their body weight and serum levels of procollagen type I N-terminal propeptide (PINP) measured one week before the start of the in-life phase (at day −7). At the beginning of the in-life phase (at day 0), animals were weighed, animals in groups 2-5 were ovariectomized, and animals in group 1 SHAM-operated. Treatment was started one day after the operations and continued once a day for two weeks (up to day 13). Sterile water was used as vehicle in groups 1 and 2. Body weight was determined at the beginning of the in-life phase (at day 0), one week after the start of the inlife phase (at day 7), and at the end of the in-life phase (at day 14). Treatment doses were adjusted according to the latest body weight obtained. After two weeks of treatment (at day 14), animals were weighed, their blood samples were harvested, animals were terminated, and their relative uterine weight was determined. For analyzing short-term effects of treatments, levels of four bone metabolism biomarkers were measured in serum samples harvested before the start of the in-life phase (at day −7) and at the end of the in-life phase (at day 14). These biochemical serum markers included PINP, N-terminal midfragment of osteocalcin (OC), C-terminal cross-linked telopeptides of type I collagen (CTX), and tartrate-resistant acid phosphatase isoform 5b (TRACP 5b). Serum levels obtained at day −7 were used as baseline levels and serum levels obtained at day 14 as levels affected by surgical operations and treatments.

Materials and Equipment

Compound 1

Solid Compound 1 was stored at room temperature in a dry environment during the entire study. Fresh dosing suspensions of Compound 1 were prepared on a daily basis. Daily aliquots of the solid compound were formulated in sterile water (Baxter, Deerfield, Ill., USA) including a small amount of hydrogen chloride (HCl; Merck KGaA, Darmstadt, Germany) as follows:

For Experimental Group 4.

4.5-5.8 mg of Compound 1 was dispersed in 22.5-29.0 ml of sterile water resulting in a dosing suspension containing 0.2 mg/ml of Compound 1. Characteristics of the formulation were improved by adding 7.5-9.7 µl of 1N HCl in the dosing suspension.

For Experimental Group 5.

10.4-17.4 mg of Compound 1 was dispersed in 17.333-29.0 ml of sterile water resulting in a dosing suspension containing 0.6 mg/ml of Compound 1. Characteristics of the formulation were improved by adding 17.3-29.0 µl of 1N HCl in the dosing suspension.

Each daily aliquot of the solid compound was mixed with sterile water by vortexing briefly. The dispersion of the compound was facilitated by sonicating in water bath (FinnSonic Ultrasonic Cleaner Model m03; FinnSonic, Lahti, Finland) for one minute followed by vortexing for five seconds. This sonication and vortexing procedure was repeated up to 3-5 times. The characteristics of the formulation were improved by adding a small amount of 1N HCl in each dosing suspension. The dispersion of the compound was facilitated further by repeating the sonication and vortexing procedure up to 1-2 times.

Fine homogenous dosing suspensions were used to treat animals in the experimental groups 4 and 5 within one hour after the compound formulation. Treatment of the animals was started one day after their surgical OVX operation (at day 1) and continued once a day for two weeks (up to day 13).

The dosing suspensions were administered orally at a volume of 5 ml/kg, resulting in an oral Compound 1 dose of 1 mg/kg/d in the experimental group 4 and an oral Compound 1 dose of 3 mg/kg/d in the experimental group 5. The dosing suspensions were mixed frequently during the administration in order to treat animals with as homogenous dosing suspensions as possible. The leftover of daily dosing suspensions were disposed properly after each administration day and the remainder of the solid Compound 1 stock after the in-life phase.

Reference Compound 17β-Estradiol

17β-estradiol (E2; Sigma-Aldrich, St. Louis, Mo., USA) was used as a reference compound in the study. The reference compound was handled according to detailed instructions provided by the supplier. Stock solution of 17β-estradiol was prepared in benzyl benzoate (Sigma-Aldrich) in a glass vial, taking care that the 17β-Estradiol was dissolved completely, as follows:

For Experimental Group 3.

1.6 mg of 17β-estradiol was dissolved in 80.0 ml of benzyl benzoate, resulting in a stock solution containing 20 µg/ml of 17β-estradiol. The stock solution was stored in its glass vial at +4° C. in dark until each daily use for two weeks. From the stock solution, a fresh dosing solution was prepared on a daily basis, as follows:

For Experimental Group 3.

1 ml of stock solution was diluted in 4 ml of castor oil (ricinus oil; lot #319108624; cat 4702.1; Carl Roth, Karlsruhe, Germany), mixed thoroughly, and kept in dark. The fresh dosing solution contained 4 µg/ml of 17β-estradiol and exhibited 20% benzyl benzoate and 80% castor oil as its vehicle composition. The solution was used to treat animals in the experimental group 3. Their treatment was started one day after their surgical OVX operation (at day 1) and continued once a day for two weeks (up to day 13). The dosing solution was administered subcutaneously at a volume of 1 ml/kg, resulting in a subcutaneous 17β-estradiol dose of 4 µg/kg/d. Left over of the daily dosing solution was disposed properly after each daily administration and the remainder of the stock solution after the in-life phase.

Vehicle

Two groups receiving test compound vehicle were included in the study, namely the experimental groups 1 and 2. The vehicle solution was sterile water and it was stored at +4° C. until each daily use for two weeks. Treatment of animals in groups 1 and 2 was started one day after their surgical operations (at day 1) and continued once a day for two weeks (up to day 13). The vehicle solution was administered orally at a volume of 5 ml/kg, resulting in an oral vehicle dose of 5 ml/kg/d. The leftover of vehicle was disposed properly after the in-life phase.

Description of the Methods Used

Biochemical markers of bone metabolism are useful tools for monitoring osteoporosis therapy and for prediction of fracture risk and long-term changes in bone mineral density (Cremers et al. 2008). In this study, serum samples were used for measuring levels of four biochemical markers of bone metabolism (Rissanen et al. 2008a, Rissanen et al. 2008b); namely PINP used as a marker of bone formation (Rat/Mouse PINP EIA; Immunodiagnostic Systems Ltd, Boldon, UK), OC used as a general marker of bone turnover (Rat-MID Osteocalcin EIA; Immunodiagnostic Systems Ltd), CTX used as a marker of bone resorption (RatLaps [CTX-I] EIA; Immunodiagnostic Systems Ltd), and TRACP 5b used as a marker of osteoclast number (RatTRAP [TRACP 5b] ELISA; Immunodiagnostic Systems Ltd). OC was used as the general marker of bone turnover, because it is secreted in the circulation both during bone formation and bone resorption (Cremers et al. 2008). The serum levels of these four biochemical markers were determined in samples harvested before the start of in-life phase of the study (at day 7) and at the end of the in-life phase (at day 14). The levels obtained at day 7 were used as baseline levels and the levels obtained at day 14 as levels affected by surgical operations and treatments. The assays were performed according to instructions provided by the supplier and their results were quantified using VICTOR2™ Multilabel Counter (PerkinElmer, Waltham, Mass., USA). Blood for serum samples was collected from the lateral tail vein after overnight fasting in order to avoid diurnal variability. The levels of PINP and TRACP 5b were measured in serum samples diluted at the ratios of 1:5 and 1:4, respectively, and the levels of OC and CTX were determined in serum without any sample dilution. Measurements of samples whose results were below or above the detection limits of the assays would have been repeated, but such results were not obtained in this study. Measurements of samples whose values were substantially different from the mean value of their experimental group would have been repeated as well, including values with a difference of more than 2.5 times the standard deviation (SD) of the group. However, these kinds of values were not obtained in this study.

Procedure

In-Life Phase of the Study

The in-life phase included animal housing and handling, surgical OVX and SHAM operations, dosing, determination of body and relative uterine weight, termination, and harvesting blood samples. Surgical OVX and SHAM operations were performed under anaesthesia and analgesia using a dorsal approach (Peng et al. 1994, Wronski et al. 1986). In OVX operation, ovaries were removed together with oviducts and a small portion of uterus. Anaesthesia was performed using medetomidine (0.6 mg/kg s.c.; CP-Pharma Handelsgesellschaft, Burhdorf, Germany), ketamine (30 mg/kg s.c.; Ketaminol; Intervetn International, Boxmeer, The Netherlands) and atipamezole (2 mg/kg s.c.; Revertor; CP-Pharma Handelsgesellschaft) injections. Postoperative analgesia was performed using buprenorphine (25-37.5 µg/kg s.c.; Temgesic; Schering-Plough, Kenilworth, N.J., USA) administered before the surgical operations and in the following morning. Carprofen (5 mg/kg s.c.) was to be used as an analgesic during the study when necessary, but was not needed. At the end of the in-life phase (at day 14), animals were terminated by asphyxication using a $CO_2$—$O_2$ mixture under anaesthesia and by subsequent cervical dislocation. The following five experimental groups were included in the study:

1) SHAM-operated control rats receiving vehicle (5 ml/kg/d p.o.)
2) OVX control rats receiving vehicle (5 ml/kg/d p.o.)
3) OVX control rats receiving 17β-estradiol (4 µg/kg/d s.c.)
4) OVX rats receiving test compound cabozantinib (1 mg/kg/d p.o.)
5) OVX rats receiving test compound cabozantinib (3 mg/kg/d p.o.)

Each group contained eight female Sprague-Dawley rats that were three months of age at the beginning of the in-life phase. The experimental design of the study is presented in FIG. 1. Health of the animals was monitored twice a day during weekdays and once a day during weekends throughout the in-life phase. Animals were allowed to acclimatize to the animal facility environment for eleven days before the start of the in-life phase. Animals were weighed and their blood samples were harvested from the lateral tail vein one week before the start of the in-life phase (at day −7). Animals were randomized to study groups by stratification according to their body weight and serum PINP levels.

Animals in poor health were not to be assigned to groups, but such animals were not observed in this study. Animals were identified by tail marks and two animals from the same experimental group were housed in each cage under controlled conditions of temperature and light and with unlimited access to tap water and a standard rat chow (Teklad Global Diet 2016; Harlan Laboratories, Madison, Wis., USA). At the beginning of the in-life phase (at day 0), animals were weighed, animals in groups 2-5 were ovariectomized, and animals in group 1 SHAM-operated. The surgical operations were performed under anaesthesia and analgesia. Treatment was started one day after the operations and continued once a day for two weeks (up to day 13). Sterile water was used as vehicle in groups 1 and 2. Body weight was determined at the beginning of the in-life phase (at day 0), one week after the start of the in-life phase (at day 7), and at the end of the in-life phase (at day 14). Treatment doses were adjusted according to the latest body weight obtained. After two treatment weeks (at day 14), animals were weighed, their blood samples were harvested, animals were terminated, and their relative uterine weight was determined.

Harvesting and Processing of Study Samples

Study samples were harvested, processed and stored as described below. All conditions that may have affected integrity of the samples and/or integrity of primary data obtained using the samples were monitored throughout the study. All samples were labelled containing at least the following information: study number, treatment group number, animal number, and sample name.

Blood Samples

Blood with a volume of 0.6 ml was harvested for serum samples before the start of in-life phase of the study (at day −7) and at the end of the in-life phase (at day 14). The blood collection was performed from the lateral tail vein after overnight fasting, and haemolysis was avoided during the blood collection and serum processing. The blood was harvested into serum gel tubes including aluminum silica as a clotting activator (Multivette 600; Sarstedt Ag & Co, Nümbrecht, Germany). After the collection of each sample, its tube was mixed gently and blood was allowed to clot for 30-60 minutes. After the clotting, the sample was centrifuged at 2500 g for 10 minutes. The resultant serum was separated and transferred to a clean sample tube. Aliquots with volumes of 30, 50, 50 and 64.1 were obtained from each sample to be used for the measurements of serum PINP, OC, CTX and TRACP 5b levels, respectively. These aliquots and the remaining serum were frozen and stored at −70° C.

Experimental Analyses

The experimental design of the study is depicted in FIG. 6. Experimental bone analyses performed in the study included measurements of serum levels of bone metabolism biomarkers. These analyses were performed by Pharmatest.

Bone Analyses

Bone analyses performed in the study included follow-up of serum levels of bone metabolism biomarkers. These biochemical markers of bone metabolism included PINP used as a marker of bone formation, OC used as a general marker of bone turnover, CTX used as a marker of bone resorption, and TRACP 5b used as a marker of osteoclast number. Their levels were determined in serum samples harvested before the start of in-life phase of the study (at day −7) and at the end of the in-life phase (at day 14). The levels obtained at day −7 were used as baseline levels and the levels obtained at day 14 as levels affected by surgical operations and treatments. Study material left over from experimental analyses All study material left over from experimental analyses is available for additional analyses and/or can be delivered to the Sponsor for further analyses at the request of the Sponsor. This material has included the remainder of the serum samples harvested during the study and stored at −70° C.

Statistical Analyses

All relevant data is presented as figures and a table (mean, SD and statistical significance) and as an appendix (individual data) with units. Values within a group that show a difference of more than two times SD from the mean value of the group and with a procedural cause for the deviation would be considered as outliers and removed from analyses. Such values were not obtained in this study.

Statistical analyses were performed with statistical software SPSS for Windows version 19 (SPSS; Chicago, Ill., USA) as two-sided tests. A p-value lower than 0.05 was considered as statistically significant. The use of transformations and non-parametric tests was decided after examining assumptions of statistical models, i.e. normality of data distribution by Shapiro-Wilk test and homogeneity of variances by Levene's test. In a case of violating these assumptions, either logarithmic or other appropriate transformation (i.e. square root and reciprocal) was applied. If the assumptions of statistical models were fulfilled as such or after transformations, differences among groups were evaluated using parametric one-way analysis of variance (ANOVA). If the one-way ANOVA revealed statistically significant differences, Dunnett's test was used for statistical comparisons between groups. If the assumptions of statistical models were not fulfilled even after transformations, non-parametric Kruskal-Wallis test was used to evaluate differences among groups. If the Kruskal-Wallis test revealed statistically significant differences, Mann-Whitney u-test was used for statistical comparisons between groups.

Follow-Up Measurements

Follow-up measurements performed in the study included the determination of body weight and measurements of serum levels of bone metabolism biomarkers. Statistical analyses of their data were performed using a relative change in each animal. For calculating the relative change during the first week of on-life phase of the study, a value obtained one week after the start of the inlife phase (at day 7) was divided by a value obtained at the beginning of the inlife phase (at day 0). For calculating the relative change during the in-life phase, a value obtained at the end of the in-life phase (at day 14) was divided by a value obtained at the beginning of the in-life phase (at day 0) or before the start of the in-life phase (at day −7).

End-Point Measurements

End-point measurements performed in the study included the determination of relative uterine weight and the determination of body weight and measurements of serum PINP levels used for randomization of animals to study groups. Statistical analyses of their data were performed using values obtained at the end of in-life phase of the study (at day 14) and one week before the start of the in-life phase (at day −7) as such.

Comparisons Between Groups

The following statistical comparisons between groups were performed:

Short-term effects of ovariectomy were studied by comparing OVX control animals treated with vehicle (group 2) with SHAM-operated control animals treated with vehicle (group 1).

Short-term effects of treatments were studied by comparing OVX animals treated with test and reference compounds (groups 3-5) with OVX control animals treated with vehicle (group 2).

Results

In this study, female Spague-Dawley rats were ovariectomized and SHAM-operated at the age of three months. Their treatment was started one day after the surgical operations, and treatment effects were followed for two weeks (in-life phase). Compound 1 (1-3 mg/kg/d p.o.) was used as test compound, 17β-estradiol (E2; 4 µg/kg/d s.c.) as reference compound and sterile water as vehicle (5 ml/kg/d p.o.). The effects of ovariectomy were studied by comparing OVX control animals treated with vehicle (group 2) with SHAM-operated control animals treated with vehicle (group 1). The effects of E2 were studied by comparing OVX control animals treated with E2 (group 3) with OVX control animals treated with vehicle (group 2). The effects of Compound 1 treatment were studied by comparing OVX animals treated with cabozantinib (groups 4-5) with OVX control animals treated with vehicle (group 2).

Tables 5a and 5b summarizes the results. An upwards arrow (↑) indicates a statistically significant increase and a downwards arrow (↓) a statistically significant decrease. One asterisk (*) indicates a statistical significance with a p-value<0.05, two asterisks () with a p-value<0.01, and three asterisks (*) with a p-value<0.001. NS=Non-significant.

According to Table 5b, The results demonstrate that surgical ovariectomy increased body weight, decreased relative uterine weight, increased serum CTX, OC and PINP levels, and decreased serum TRACP 5b activity in female rats two weeks after the ovariectomy.

TABLE 5a

Short-term Effects of Compound 1 on Body Weight in the Rat OVX Model

| METHOD/PARAMETER | OVX | E2 4 µg/kg/d s.c. | cabozantinib (mg/kg/d p.o.) | |
|---|---|---|---|---|
| | | | 1 | 3 |
| BODY WEIGHT | | | | |
| Body weight, change | | | | |
| During the first week | ↑ ** | ↓ ** | ↓ * | NS |
| During the in-life phase | ↑ ** | ↓ ** | ↓ * | NS |
| RELATIVE UTERINE WEIGHT | | | | |
| Relative uterine weight at day 14 | ↓ ** | ↑ ** | NS | NS |

TABLE 5a

Short-term Effects of Compound 1 on Bone Metabolism Biomarkers in the Rat OVX Model

| METHOD/PARAMETER | OVX | E2 4 µg/kg/d s.c. | cabozantinib (mg/kg/d p.o.) 1 | 3 |
|---|---|---|---|---|
| BIOCHEMICAL MARKERS OF BONE METABOLISM Serum PINP levels, change | | | | |
| During the in-life phase Serum OC levels, change | ↑ ** | ↓ ** | NS | ↑ * |
| During the in-life phase Serum CTX levels, change | ↑ * | ↓ *** | NS | NS |
| During the in-life phase Serum TRACP 5b activity, change | ↑ ** | ↓ *** | NS | NS |
| During the in-life phase | ↓ *** | NS | NS | ↓ * |

The biomarker results indicate that surgical ovariectomy enhanced bone resorption, increased bone turnover and bone formation, and decreased the total number of osteoclasts. The conclusions imply that the ovariectomy accelerated the rate of bone turnover in female rats. The results describing the short-term effects of ovariectomy are in line with results published in the literature demonstrating that the present study can be used to evaluate the preclinical efficacy of therapies in OVX rats (Rissanen et al. 2008a, Rissanen et al. 2008b).

As indicated, The bone metabolism biomarker results indicate that treatment with Compound 1 at the oral dose of 3 mg/kg/d enhanced the OVX-induced increase in bone formation and the OVX-induced reduction in the total number of osteoclasts, but did not affect the OVX-induced increase in bone resorption and bone turnover in OVX rats after two weeks of treatment. The enhanced bone formation in association with the reduced total number of osteoclasts and the unaltered levels of bone resorption imply that treatment with Compound 1 at the oral dose of 3 mg/kg/d shifted the OVX-stimulated bone turnover towards bone formation in female rats.

REFERENCES

Lindsay R and Cosman F (2008) The pharmacology of estrogens in osteoporosis. In: Bilezikian J P, Raisz L G and Martin T J (eds.) Principles of bone biology. Academic Press, San Diego, Calif., USA, pp. 1769-75.
Raisz L G, Bilezikian J P and Martin T J (2008) Pathophysiology of osteoporosis. In: Bilezikian J P, Raisz L G and Martin T J (eds.) Principles of bone biology. Academic Press, San Diego, Calif., USA, pp. 1635-47.
Rissanen J P and Halleen J M (2010) Models and screening assays for drug discovery in osteoporosis. Expert Opin Drug Discov. 5: 1163-74.
Cremers S, Garnero P and Seibel M J (2008) Biochemical markers of bone metabolism. In: Bilezikian J P, Raisz L G and Martin T J (eds.) Principles of bone biology. Academic Press, San Diego, Calif., USA, pp. 1857-81.
Rissanen J P, Suominen M I, Peng Z and Halleen J M (2008a) Secreted tartrate-resistant acid phosphatase 5b is a marker of osteoclast number in human osteoclast cultures and the rat ovariectomy model. Calcif Tissue Int. 82: 108-15.
Rissanen J P, Suominen M I, Peng Z, Morko J, Rasi S, Risteli J and Halleen J M (2008b) Short-term changes in serum PINP predict long-term changes in trabecular bone in the rat ovariectomy model. Calcif Tissue Int. 82: 155-61.
Peng Z, Tuukkanen J, Zhang H, Jämsä T and Väänänen HK (1994) The mechanical strength of bone in different rat models of experimental osteoporosis. Bone. 15: 523-32.
Wronski T J, Walsh C C and Ignaszewski L A (1986) Histologic evidence for osteopenia and increased bone turnover in ovariectomized rats. Bone. 7: 119-23.

Other Embodiments

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive.

The scope of the invention should, therefore, be determined not with reference to the above description, but should instead be determined with reference to the following appended claims, along with the full scope of equivalents to which such claims are entitled.

The invention claimed is:

1. A method for treating osteoporosis, comprising administering to a patient in need of such treatment a once daily dose of 15, 10, or 5 mg of Compound 1:

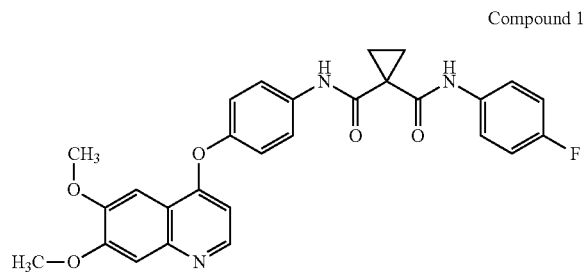 [SMILES: COc1cc2nccc(Oc3ccc(NC(=O)C4(C(=O)Nc5ccc(F)cc5)CC4)cc3)c2cc1OC]

Compound 1

N-(4-{[6,7-bis(methyloxy)quinolin-4-yl]oxy}phenyl)-N-(4-fluorophenyl)cyclopropane-1,1-dicarboxamide or a pharmaceutically acceptable salt thereof; wherein Compound 1 stimulates osteoblast differentiation and inhibits osteoclast differentiation.

2. The method of claim 1, wherein Compound 1 is the (L)-malate salt.

3. The method of claim 1, wherein Compound 1, or a pharmaceutically acceptable salt thereof, is administered as a pharmaceutical composition comprising a pharmaceutically acceptable carrier.

4. A method for treating osteoporosis in patients who have or are currently undergoing treatment for cancer, comprising administering a once daily dose of 15, 10, or 5 mg of Compound 1:

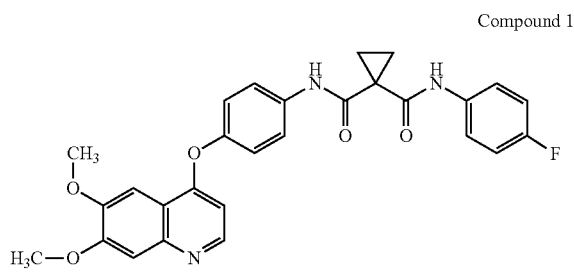 [SMILES: COc1cc2nccc(Oc3ccc(NC(=O)C4(C(=O)Nc5ccc(F)cc5)CC4)cc3)c2cc1OC]
Compound 1 or the malate salt of Compound 1; wherein Compound 1 stimulates osteoblast differentiation and inhibits osteoclast differentiation.

5. A method for ameliorating abnormal deposition of unstructured bone accompanied by increased skeletal fractures, spinal cord compression, and severe bone pain of osteoporosis, comprising administering to a patient in need of such treatment a once daily dose of 15, 10, or 5 mg of Compound 1:

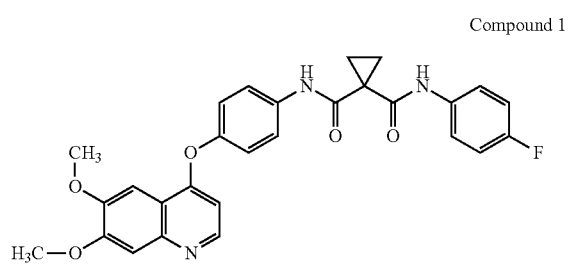 [SMILES: COc1cc2nccc(Oc3ccc(NC(=O)C4(C(=O)Nc5ccc(F)cc5)CC4)cc3)c2cc1OC]
Compound 1 or the malate salt of Compound 1; wherein Compound 1 stimulates osteoblast differentiation and inhibits osteoclast differentiation.

6. A method for stimulating osteoblast differentiation and/or activity in a patient with osteoporosis in need of such treatment, comprising administering to the patient a once daily dose of 15, 10, or 5 mg of Compound 1:

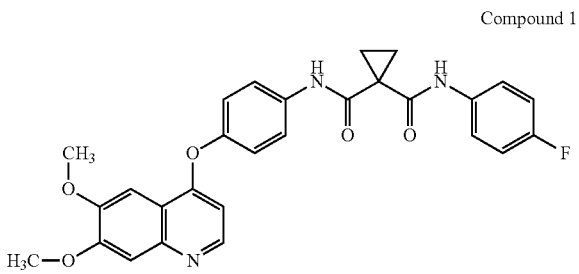 [SMILES: COc1cc2nccc(Oc3ccc(NC(=O)C4(C(=O)Nc5ccc(F)cc5)CC4)cc3)c2cc1OC]
Compound 1 or the malate salt of Compound 1; wherein Compound 1 stimulates osteoblast differentiation and inhibits osteoclast differentiation.

7. A method for stimulating bone formation in a patient with osteoporosis in need of such treatment, comprising administering to the patient a once daily dose of 15, 10, or 5 mg of Compound 1:

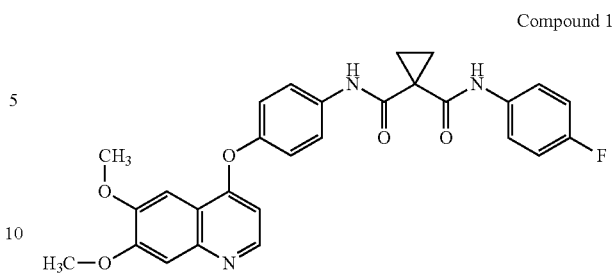
Compound 1 or the malate salt of Compound 1; wherein Compound 1 stimulates osteoblast differentiation and inhibits osteoclast differentiation.

8. A method for inhibiting osteoclast differentiation and/or activity in a patient with osteoporosis in need of such treatment, comprising administering to the patient a once daily dose of 15, 10, or 5 mg of Compound 1:

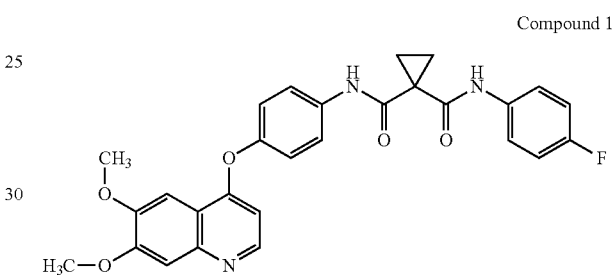
Compound 1 or the malate salt of Compound 1; wherein Compound 1 stimulates osteoblast differentiation and inhibits osteoclast differentiation.

9. A method for modulating bone turnover toward bone formation in a patient with osteoporosis in need of such treatment, comprising administering to the patient a once daily dose of 15, 10, or 5 mg of Compound 1:

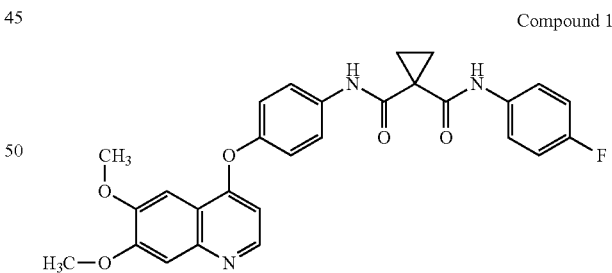
Compound 1 or the malate salt of Compound 1 or another pharmaceutically acceptable salt of Compound 1; wherein Compound 1 stimulates osteoblast differentiation and inhibits osteoclast differentiation.

* * * * *